US011567069B2

(12) United States Patent
Kanno et al.

(10) Patent No.: US 11,567,069 B2
(45) Date of Patent: Jan. 31, 2023

(54) METAL MICROSCOPIC STRUCTURE AND DETECTION DEVICE

(71) Applicant: Panasonic Intellectual Property Management Co., Ltd., Osaka (JP)

(72) Inventors: Takashi Kanno, Hyogo (JP); Hiroto Yanagawa, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 117 days.

(21) Appl. No.: 17/071,578

(22) Filed: Oct. 15, 2020

(65) Prior Publication Data

US 2021/0025884 A1 Jan. 28, 2021

Related U.S. Application Data

(63) Continuation of application No. PCT/JP2019/025629, filed on Jun. 27, 2019.

(30) Foreign Application Priority Data

Aug. 24, 2018 (JP) .............................. JP2018-157377

(51) Int. Cl.
*G01N 33/543* (2006.01)
*G01N 21/64* (2006.01)
(Continued)

(52) U.S. Cl.
CPC ..... *G01N 33/54386* (2013.01); *G01N 21/648* (2013.01); *G01N 21/6428* (2013.01);
(Continued)

(58) Field of Classification Search
CPC ......... G01N 33/54386; G01N 21/6428; G01N 21/6458; G01N 21/648; G01N 33/54373;
(Continued)

(56) References Cited

U.S. PATENT DOCUMENTS

2014/0099732 A1* 4/2014 Walavalkar ............ G01N 21/63
422/69
2015/0233832 A1 8/2015 Maruyama et al.
(Continued)

FOREIGN PATENT DOCUMENTS

JP 2007-240361 9/2007
JP 2008-196898 8/2008
(Continued)

OTHER PUBLICATIONS

Tawa et al., "Application of 300x Enhanced Fluorescence on a Plasmonic Chip Modified with a Bispecific Antibody to a Sensitive Immunosensor", 2013, ACS Appl. Mater. Interfaces, 5, 17, 8628-8632 (Year: 2013).*
(Continued)

*Primary Examiner* — Samuel P Siefke
*Assistant Examiner* — Henry H Nguyen
(74) *Attorney, Agent, or Firm* — McDermott Will & Emery LLP

(57) ABSTRACT

One non-limiting and exemplary embodiment provides a metal microscopic structure capable of detecting a low-concentration analyte with high sensitivity. The metal microscopic structure includes a base member including multiple
(Continued)

protrusions arrayed at predetermined intervals, and multiple projections made of a metal film covering the base member and configured to generate surface plasmons upon irradiation with light. A film thickness of the metal film positioned in a bottom portion of a gap between every adjacent two of the multiple projections is greater than a height of the multiple protrusions and is more than or equal to 90% and less than or equal to 100% of a film thickness of the metal film deposited on top portions of the multiple protrusions.

13 Claims, 9 Drawing Sheets

(51) Int. Cl.
  *G01N 33/553* (2006.01)
  *B82Y 15/00* (2011.01)
  *G02B 5/00* (2006.01)

(52) U.S. Cl.
  CPC ... *G01N 21/6458* (2013.01); *G01N 33/54373* (2013.01); *G01N 33/553* (2013.01); *G02B 5/008* (2013.01); *B82Y 15/00* (2013.01); *G01N 2021/6441* (2013.01); *G01N 2333/005* (2013.01)

(58) Field of Classification Search
  CPC ......... G01N 33/553; G01N 2021/6441; G01N 2333/005; G02B 5/008; B82Y 15/00
  See application file for complete search history.

(56) References Cited

U.S. PATENT DOCUMENTS

| | | |
|---|---|---|
| 2017/0219488 A1 | 8/2017 | Fukuda et al. |
| 2018/0073065 A1 | 3/2018 | Bowen et al. |
| 2020/0158723 A1 | 5/2020 | Yanagawa |

FOREIGN PATENT DOCUMENTS

| | | |
|---|---|---|
| JP | 2014-160021 | 9/2014 |
| JP | 2015-014545 | 1/2015 |
| JP | 2015-014547 | 1/2015 |
| JP | 2015-052562 | 3/2015 |
| JP | 2016-020887 | 2/2016 |
| JP | 2017-503483 | 2/2017 |
| JP | 2017-181308 | 10/2017 |
| WO | 2016/021516 | 2/2016 |
| WO | 2019/069717 | 4/2019 |

OTHER PUBLICATIONS

Chang et al., "Detection of swine-origin influenza A (H1N1) viruses using a localized surface plasmon coupled fluorescence fiber-optic biosensor", 2010, Biosensors and Bioelectronics, 26, 3, 1068-1073 (Year: 2010).*

Translation of JP2008196898A, Kusunoki, Fuminori, Aug. 28, 2008 (Year: 2008).*

International Search Report of PCT application No. PCT/JP2019/025629 dated Sep. 17, 2019.

Jaeyoung Yang et al., "Surface-Enhanced Raman Spectroscopy Based Quantitative Bioassay on Aptamer-Functionalized Nanopillars Using Large-Area Raman Mapping", ACS NANO 2013, vol. 7, No. 6, 5350-5359, May 28, 2013.

* cited by examiner

METAL MICROSCOPIC STRUCTURE AND DETECTION DEVICE

BACKGROUND

1. Technical Field

The present disclosure relates to a metal microscopic structure for use in detection of light such as surface-enhanced fluorescence, for example, and to a virus detection device using the metal microscopic structure.

2. Description of the Related Art

Optical detection methods utilizing surface-enhanced Raman spectroscopy or surface-enhanced fluorometry, for example, are known as techniques for collecting virus particles floating in the air and optically measuring the collected virus particles.

A plasmonic substrate including a metal microscopic structure is used in a sensor device utilizing the surface-enhanced fluorescence. As techniques for manufacturing such a sensor device, there are disclosed a technique of periodically arranging metal microscopic protrusions on a substrate (for example, Japanese Unexamined Patent Application Publication No. 2008-196898), a technique of periodically arranging metal balls on a substrate (for example, Japanese Unexamined Patent Application Publication No. 2016-20887), and a technique of periodically arranging recesses (for example, Japanese Unexamined Patent Application Publication No. 2014-160021). Japanese Unexamined Patent Application Publication No. 2015-014545 discloses a surface-enhanced Raman scattering element and a manufacturing method for the same.

SUMMARY

However, the above-described metal microscopic structures of the related art cannot detect a low-concentration analyte due to structural problems in some cases.

One non-limiting and exemplary embodiment provides a metal microscopic structure capable of detecting a low-concentration analyte with high sensitivity, and a detection device using the metal microscopic structure.

In one general aspect, the techniques disclosed here feature a metal microscopic structure comprising a base member including multiple protrusions arrayed at predetermined intervals, and multiple projections made of a metal film covering the base member and configured to generate surface plasmons upon irradiation with light, wherein a film thickness of the metal film positioned in a bottom portion of a gap between every adjacent two of the multiple projections is greater than a height of the multiple protrusions and is more than or equal to 90% and less than or equal to 100% of a film thickness of the metal film deposited on top portions of the multiple protrusions.

According to the present disclosure, a low-concentration analyte can be detected with high sensitivity.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
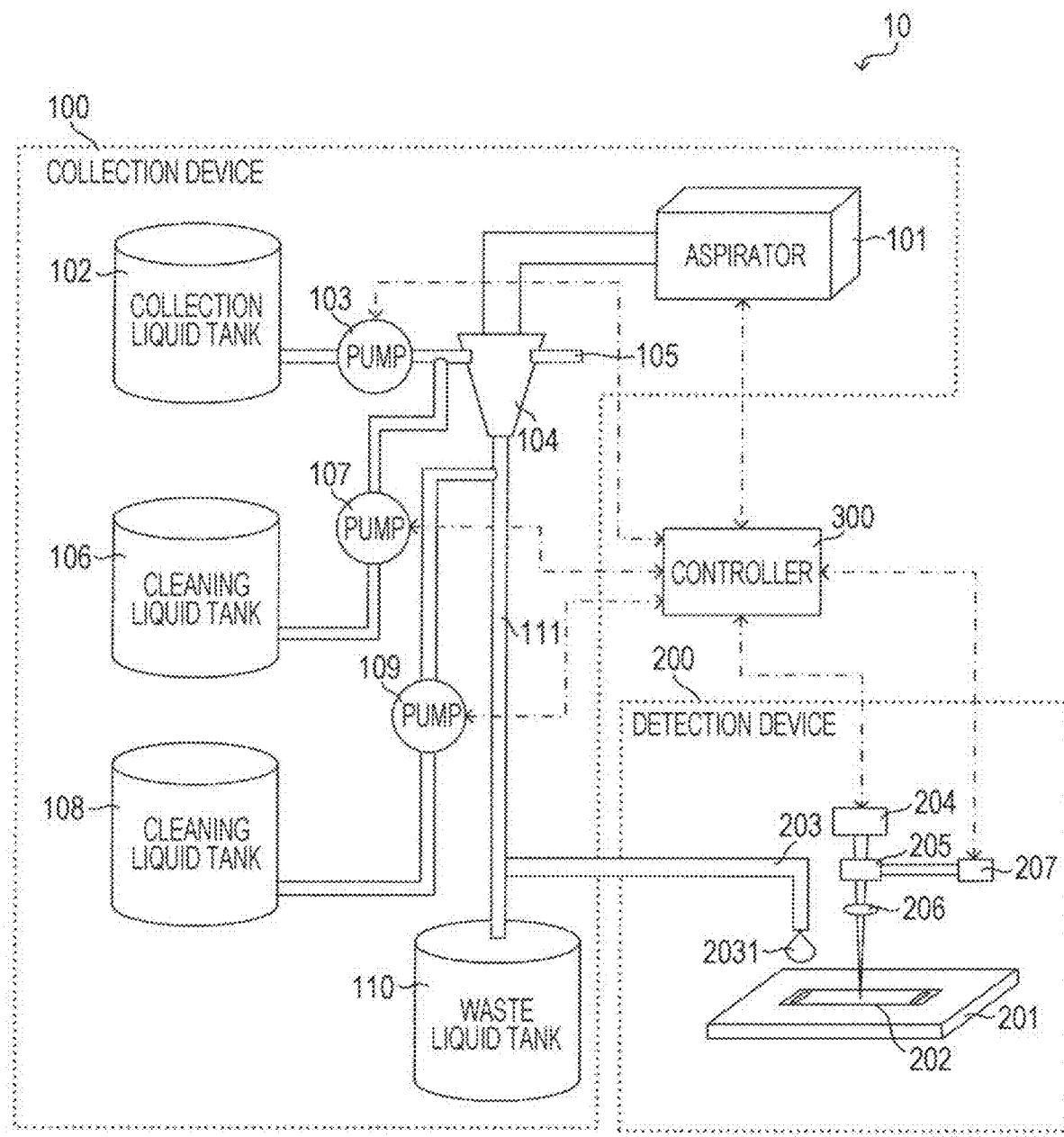
FIG. 1 is a block diagram illustrating an example of a detection system according to an embodiment.

In one aspect, the present disclosure is summarized as follows.

A metal microscopic structure according to the one aspect of the present disclosure comprises a base member including multiple protrusions arrayed at predetermined intervals, and multiple projections made of a metal film covering the base member and configured to generate surface plasmons upon irradiation with light, wherein a film thickness of the metal film positioned in a bottom portion of a gap between every adjacent two of the multiple projections is greater than a height of the multiple protrusions and is more than or equal to 90% and less than or equal to 100% of a film thickness of the metal film deposited on top portions of the multiple protrusions.

With the above-described feature, since the film thickness of the metal film deposited on the top portions of the protrusions is thicker than the film thickness of the metal film positioned in the bottom portion of the gap between every adjacent two of the projections, the relevant gap has a larger depth. Because the surface plasmons are enhanced in the gap, the larger depth of the gap increases a region where the surface plasmons are generated. With the metal microscopic structure according to the one aspect of the present disclosure, therefore, a larger number of bound bodies each being a combination of an analyte and a luminous body can be caused to stay in the region where the surface plasmons are generated. Accordingly, the metal microscopic structure according to the one aspect of the present disclosure can detect the low-concentration analyte with high accuracy. Furthermore, since the film thickness of the metal film positioned in the bottom portion of the gap between every adjacent two of the projections is greater than the height of the protrusions, the protrusions are completely covered with the metal film. In addition, a sufficient thickness is ensured as the film thickness of the metal film positioned in the bottom portion of the above-mentioned gap. Accordingly, the metal microscopic structure is less susceptible to the influence of the base member at the location where the film thickness is most likely to become thin, and can exhibit a stable optical electric-field enhancement effect, namely a stable plasmon characteristic. As a result, the metal microscopic structure according to the one aspect of the present disclosure can detect the low-concentration analyte with high accuracy.

In the metal microscopic structure according to the one aspect of the present disclosure, for example, a vertical sectional shape of each of the multiple projections may be a forward tapered shape.

With the above-described feature, since the gap between every adjacent two of the projections is wider on a top portion side of the projections, the bound body of the analyte and the luminous body is more likely to enter the gap. Therefore, a proportion of the bound body entering the gap can be increased. Furthermore, the gap between every adjacent two of the projections gradually narrows toward the bottom portion of the gap. For example, when a width of the gap is minimized in the bottom portion of the gap, the optical electric-field enhancement effect is maximized in the bottom portion of the gap. Since the gap gradually narrows toward the bottom portion of the gap, the bound body is more likely to reach the bottom portion of the gap, and a larger number of the bound bodies are more likely to be held in the bottom portion of the gap. In other words, a larger number of the bound bodies can be held in the region where the optical electric-field enhancement effect is maximized. As a result, the metal microscopic structure according to the one aspect of the present disclosure can detect the low-concentration analyte with higher sensitivity.

In the metal microscopic structure according to the one aspect of the present disclosure, for example, the base member may be made of resin, each of the multiple protrusions may have a circular columnar shape, the multiple protrusions may be arranged in a form of regular triangle lattices in a plan view, a thickness of the multiple protrusions may be more than or equal to 184 nm and less than or equal to 276 nm, and an interval between every adjacent two of the multiple protrusions may be more than or equal to 184 nm and less than or equal to 276 nm.

Since the base member is made of resin as described above, the protrusions can easily be formed in the desired shape and at the desired interval. Furthermore, since the protrusions have the circular columnar shape and are arranged in the form of regular triangle lattices in a plan view, the multiple projections with a uniform lattice period can be formed when the multiple protrusions are covered with the metal film. In addition, since the thickness of the protrusions and the interval between every adjacent two of the protrusions are each in the above-mentioned range, the uniform metal microscopic structure can be obtained when the protrusions are covered with the metal film.

In the metal microscopic structure according to the one aspect of the present disclosure, the height of each of the multiple protrusions may be more than or equal to 160 nm and less than or equal to 240 nm, and the film thickness of the metal film positioned in the bottom portion of the gap between every adjacent two of the multiple projections may be more than or equal to 200 nm and less than or equal to 600 nm.

With the above-described feature, since the film thickness of the metal film positioned in the bottom portion of the gap between every adjacent two of the projections is greater than the height of each of the protrusions, the protrusions are completely covered with the metal film. In addition, a sufficient thickness is ensured as the film thickness of the metal film positioned in the bottom portion of the above-mentioned gap. Accordingly, the metal microscopic structure is less susceptible to the influence of the base member at the location where the film thickness is most likely to become thin, and can exhibit the stable optical electric-field enhancement effect.

In the metal microscopic structure according to the one aspect of the present disclosure, an interval between every adjacent two of the multiple projections is more than or equal to 40 nm and less than or equal to 120 nm on a top portion side of the multiple projections in a cross section that passes a center of each of the multiple projections in a plan view and that is perpendicular to the base member, and the interval is more than or equal to 10 nm and less than or equal to 40 nm on a bottom portion side of the multiple projections.

With the above-described feature, since the gap between every adjacent two of the projections is wider on the top portion side of the projections, the bound body of the analyte and the luminous body is more likely to enter the gap. Therefore, a proportion of the bound body entering the gap can be increased. Furthermore, the gap between every adjacent two of the projections gradually narrows toward the bottom portion side of the projections, namely the bottom portion side of the gap. For example, when the width of the gap is minimized in the bottom portion of the gap, the optical electric-field enhancement effect is maximized in the bottom portion of the gap. Since the gap gradually narrows toward the bottom portion side of the gap, the bound body is more likely to reach the bottom portion of the gap, and a larger number of the bound bodies are more likely to be held in the bottom portion of the gap. In other words, a larger number of the bound bodies can be held in the region where the optical electric-field enhancement effect is maximized. For example, when a bound body is formed by binding the analyte and a labeled antibody that is obtained by modifying a VHH (variable domain of heavy chain of heavy-chain antibody) antibody with a fluorescent substance, the VHH antibody specifically binding to the analyte, the bound body has a length of smaller than 10 nm. Even in such a case, since the above-mentioned gap is more than or equal to 10 nm on the bottom portion side of the projections, it is also possible to hold a larger number of the bound bodies in the bottom portion of the gap, namely in the region where the optical electric-field enhancement effect is maximized. As a result, the metal microscopic structure according to the one aspect of the present disclosure can detect the low-concentration analyte with higher sensitivity.

In the metal microscopic structure according to the one aspect of the present disclosure, for example, the metal film may be made of gold, silver, copper, aluminum, or an alloy containing gold, silver, copper, or aluminum as a main component.

With the above-described feature, the resonance wavelength of the surface plasmon resonance can be controlled to a wavelength in the desired wavelength range. More specifically, in consideration of that the resonance wavelength of the surface plasmon resonance is different depending on the type of metal, the metal film can be formed by selecting the desired one from among the above-mentioned materials of the metal film in match with the fluorescent wavelength of the luminous body, for example, a fluorescent substance, that is used to detect the analyte.

A detection device according to another aspect of the present disclosure comprises the above-described metal microscopic structure, an inlet guide configured to introduce both a sample possibly containing an analyte and a luminous body to the metal microscopic structure, a light source capable of emitting light with which the metal microscopic structure and a bound body of the analyte and the luminous body are irradiated, and an optical detector configured to detect light emitted from the luminous body that has been excited by the light emitted from the light source.

With the above-described feature, the detection device according to the other aspect of the present disclosure introduces the bound body of the analyte and the luminous body to the metal microscopic structure, irradiates the metal microscopic structure and the bound body having been introduced to the metal microscopic structure with light, and detects light emitted from the luminous body that has been excited by the light for the irradiation. Therefore, the detection device according to the other aspect of the present disclosure can detect and quantitate the analyte by detecting the light emitted from the luminous bodies.

The detection device according to the other aspect of the present disclosure may further include a first antibody that has a property of specifically binding to the analyte and that has been immobilized onto the metal microscopic structure, wherein the analyte is a virus or a component of the virus, and a second antibody that has a property of specifically binding to the analyte specifically bound to the first antibody and that has been labeled with the luminous body.

With the above-described feature, since the analyte specifically binds to the first antibody that has been immobilized onto the metal microscopic structure, the analyte can be held on the metal microscopic structure with the first antibody interposed therebetween. Accordingly, the analyte can be more reliably held on the metal microscopic structure. In addition, since the second antibody labeled with the luminous body specifically binds to the analyte, the luminous body can be bound to the analyte, which has been held on the metal microscopic structure, with the second antibody interposed therebetween. This enables the luminous body to be more reliably bound to the analyte. As a result, the detection device according to the other aspect of the present disclosure can detect the analyte, namely the virus or the virus component, with high sensitivity.

In the detection device according to the other aspect of the present disclosure, the wavelength of the light emitted from the light source may be longer than or equal to 400 nm and shorter than or equal to 850 nm, and the wavelength of the light detected by the optical detector may be longer than or equal to 400 nm and shorter than or equal to 850 nm.

With the above-described feature, when the luminous body is a fluorescent substance, for example, it is possible to use the fluorescent substance satisfying the conditions that the wavelength of light absorbed by the fluorescent substance is in the range of longer than or equal to 400 nm and shorter than or equal to 850 nm, and that the wavelength of fluorescence emitted from the fluorescent substance is in the range of longer than or equal to 400 nm and shorter than or equal to 850 nm. Accordingly, the detection sensitivity can be increased by suppressing the emission of autofluorescence from a substance, for example, a VHH antibody, contained in the analyte. Hence the above-described feature enables a small amount of the analyte to be detected with high sensitivity.

Embodiments of the present disclosure will be described below with reference to the drawings.

It is to be noted that any of the embodiments described below represents a generic or specific example, Numerical values, shapes, materials, components, arrangement positions and connection forms of the components, steps, sequences of steps, and so on, which are described in the following embodiments, are merely illustrative, and they are not purported to limit the scope of Claims. Among the components in the following embodiments, those ones other than the components not stated in independent claims, which define the most significant concepts, are described as optional components.

The drawings are not always exactly depicted in a strict sense. Throughout the drawings, substantially the same components are denoted by the same reference sings in the drawings, and duplicate description of those components is omitted or simplified.

Coordinate axes are indicated in some of the drawings referenced in description of the following embodiments. The Z-direction in the coordinate axes is a direction perpendicular to a principal surface of a sensor substrate. The X-direction and the Y-direction are directions orthogonal to each other on a plane that is perpendicular to the Z-direction. The X-Y plane is a plane parallel to the principal surface of the sensor substrate. In the following embodiments, for example, the wording "in a plan view" implies "when viewed from the Z-direction".

Furthermore, in this specification, terms representing relations between elements, such as "parallel", terms representing shapes of elements, such as "rectangle", numerical values, and ranges of numerical values are expressions that are not always used to imply the strictly exact meanings and that include allowances covering substantially identical ranges, for example, differences of about several percent.

EMBODIMENTS

Outline of Detection System

A metal microscopic structure and a detection device according to an embodiment may be each, for example, a component of a detection system described below. FIG. 1 is a block diagram illustrating an example of a detection system 10 according to the embodiment. The detection system 10 is installed in a room for people to enter and exit. The detection system 10 collects, for example, fine particles possibly containing an analyte, such as a virus floating in the air, and detects the concentration of the analyte contained in the fine particles. This embodiment is described in connection with the case in which the analyte is a virus or a virus component (hereinafter simply called a "virus"). The virus component is, for example, a protein or a nucleic acid forming the virus. The type of virus is not limited to particular one, and may be what is generally classified as a virus. The analyte needs not to be the virus, and may be, for example, a bacterium or an allergen such as pollen.

As illustrated in FIG. 1, the detection system 10 includes a collection device 100, a detection device 200, and a controller 300. Details of the collection device 100, the detection device 200, and the controller 300 will be described below.

Configuration of Collection Device

The collection device 100 collects the fine particles possibly containing the analyte in the air, and mixes the collected fine particles into a collection liquid. More specifically, the collection device 100 sucks the ambient atmospheric air through an air inlet 105, collects the fine particles possibly containing the virus or the likes in the air, and mixes the collected fine particles into the collection liquid, thereby collecting virus particles in the air. As illustrated in FIG. 1, the collection device 100 includes an aspirator 101, a collection liquid tank 102, a pump 103, a cyclone 104, the air inlet 105, a cleaning liquid tank 106, a pump 107, a cleaning liquid tank 108, a pump 109, a waste liquid tank 110, and a liquid flow path 111. Those components of the collection device 100 will be described below.

The aspirator 101 sucks the ambient atmospheric air through the air inlet 105. The fine particles possibly containing the virus floating in the ambient atmospheric air are thereby sucked into the cyclone 104 through the air inlet 105 together with the air. The aspirator 101 is connected to the cyclone 104 and is driven to operate the cyclone 104.

The collection liquid tank 102 is a container for containing a collection liquid to collect the viruses in the air.

The pump 103 supplies the collection liquid in the collection liquid tank 102 to the cyclone 104.

The cyclone 104 is connected to the air inlet 105 and the collection liquid tank 102, and mixes the fine particles possibly containing the virus in the air that has been sucked by the aspirator 101 through the air inlet 105, with the collection liquid supplied from the collection liquid tank 102 by the pump 103. In other words, the cyclone 104 mixes the fine particles possibly containing the virus in the sucked air into the collection liquid. Thus the cyclone 104 prepares the collection liquid mixed with the fine particles (hereinafter called a "sample") by mixing the sucked fine particles and the collection liquid. The cyclone 104 is connected to the detection device 200 via the liquid flow path 111. The sample is supplied from the cyclone 104 to the detection device 200 via the liquid flow path 111.

The cleaning liquid tank 106 is a container for containing a cleaning liquid to clean the cyclone 104 and the liquid flow path 111. The cleaning liquid tank 106 is connected to the cyclone 104, and the cleaning liquid in the cleaning liquid tank 106 is supplied to the cyclone 104 by the pump 107.

The cleaning liquid tank 108 is a container for containing a cleaning liquid to clean the liquid flow path 111. The cleaning liquid tank 108 is connected to the liquid flow path 111, and the cleaning liquid in the cleaning liquid tank 108 is supplied to the liquid flow path 111 by the pump 109.

The waste liquid tank 110 is a container for storing useless liquids. The waste liquid tank 110 stores, for example, the cleaning liquids after having been used to clean the cyclone 104 and the liquid flow path 111.

The liquid flow path 111 is a path through which the sample discharged from the cyclone 104 is introduced to the detection device 200. The liquid flow path 111 is connected to an inlet guide 203 of the detection device 200.

Configuration of Detection Device

Figure 2:
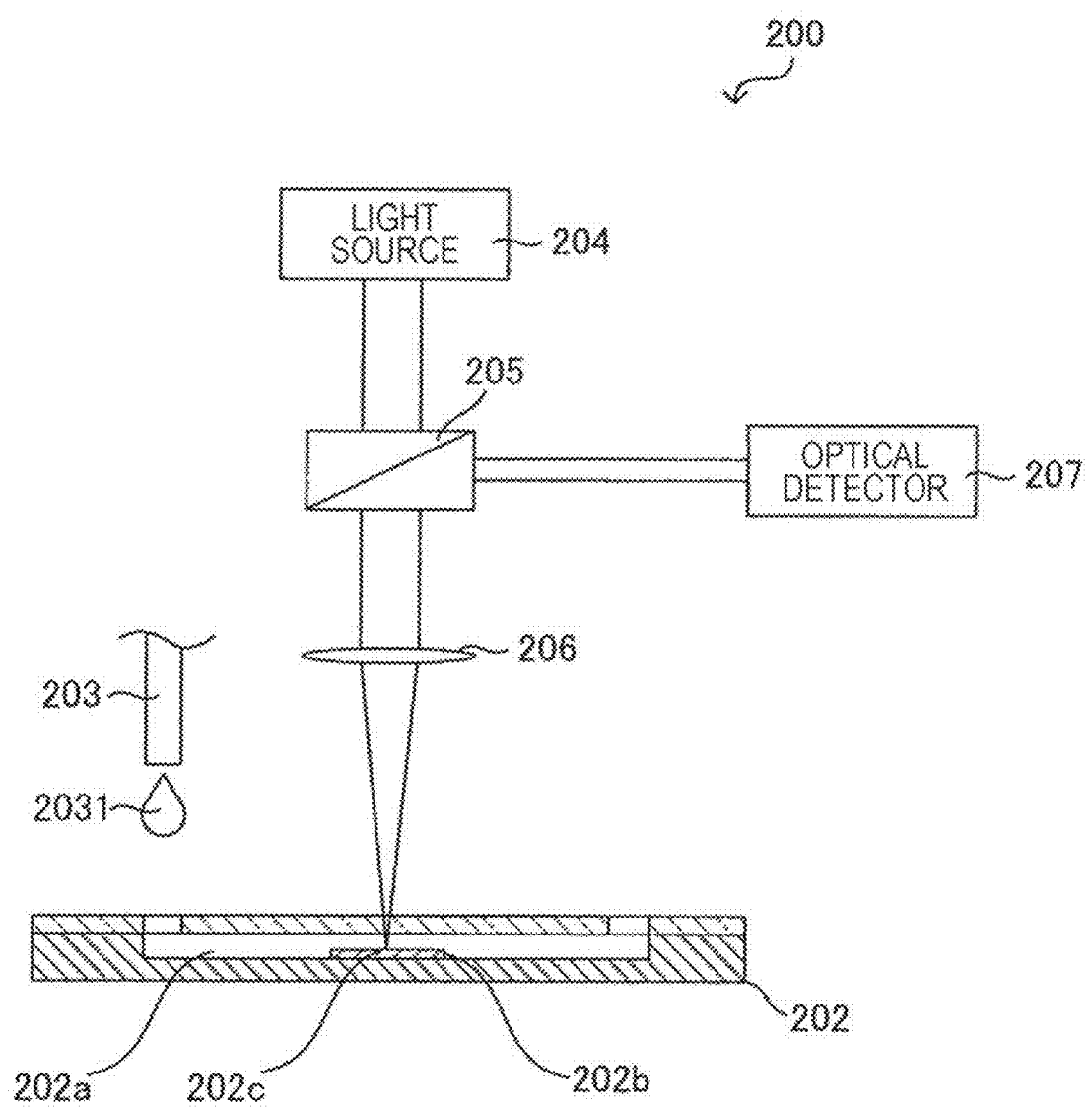
FIG. 2 is a schematic view illustrating an example of a detection device according to the embodiment.

The detection device 200 will be described in detail below with reference to FIGS. 1 and 2. FIG. 2 is a schematic view illustrating an example of the detection device 200 according to this embodiment.

The detection device 200 according to the embodiment includes a metal microscopic structure 2021, the inlet guide 203 that introduces both the sample possibly containing the virus and a luminous body to the metal microscopic structure 2021, a light source 204 capable of emitting light with which the metal microscopic structure 2021 and a bound body of the virus and the luminous body are irradiated, and an optical detector 207 configured to detect light emitted from the luminous body that has been excited by the light emitted from the light source 204. The luminous body is a substance emitting light when excited upon irradiation with light of a predetermined wavelength, and the luminous body is, or example, a fluorescent substance. The following description is made in connection with the case in which the luminous body is the fluorescent substance.

The detection device 200 detects the virus from the collection liquid into which the fine particles have been mixed in the collection device 100. As illustrated in FIGS. 1 and 2, the detection device 200 includes a sensor device 201, the inlet guide 203, the light source 204, a lens 206, a beam splitter 205, and the optical detector 207. The individual components of the detection device 200 will be described below.

The sensor device 201 includes a sensor cell 202. Although, in FIG. 1, the sensor device 201 includes one sensor cell 202, the sensor device is not limited to such an example. In another example, the sensor device 201 may include multiple sensor cells 202. The shape of the sensor device 201 is not limited to a particular one and may be rectangular or disk-shaped.

In this embodiment, when the analyte is the virus or the virus component, for example, the sensor device 201 can measure the number of virus particles (in the range of $10^3$ to $10^6$) in a sample liquid 2031 of a predetermined volume (for example, 1 ml). When the analyte is a biological substance such as an enzyme or an immune antibody, for example, the sensor device 201 can measure the concentration of the biological substance in the sample liquid 2031 of a predetermined volume. In the detection device 200 according to this embodiment, the surface-enhanced fluorometry is utilized to optically detect the analyte.

As illustrated in FIG. 2, the sensor cell 202 includes a flow channel 202a and a sensor substrate 202b.

The flow channel 202a introduces the sample liquid 2031 dropped from the inlet guide 203 to a detection region 202c. The flow channel 202a has a supply hole through which the sample liquid 2031 is supplied to the inside of the flow channel 202a, and a discharge hole through which the sample liquid 2031 in the flow channel 202a is discharged to the outside of the sensor cell 202. Thus, in the sensor cell 202, a set of the supply hole and the discharge hole are communicated with one corresponding flow channel 202a.

Figure 3A:
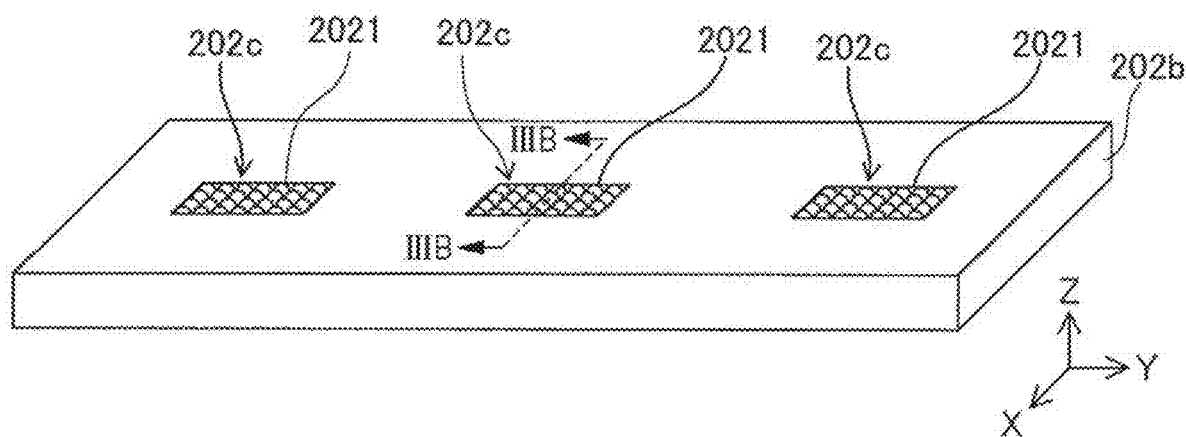
FIG. 3A is a perspective view illustrating an example of a sensor substrate in the embodiment.

FIG. 3A is a perspective view illustrating an example of the sensor substrate 202b in the embodiment. As illustrated in FIGS. 2 and 3A, the sensor substrate 202b includes the detection region 202c. The detection region 202c is a region where the virus is optically detected with the aid of surface plasmons. The metal microscopic structure 2021 is disposed in the detection region 202c. When the detection region 202c is irradiated with the excitation light from the light source 204, metal particles forming the metal microscopic structure 2021 are excited and the surface plasmons are generated on the surface of a metal film of the metal microscopic structure 2021. Accordingly, the intensity of light (hereinafter called "fluorescence") emitted from the florescent substance bound to the virus is enhanced. For example, when the sample liquid 2031 is introduced to the detection region 202c and the metal microscopic structure 2021 and the bound body of the virus and the florescent substance are irradiated with the excitation light from the light source 204, the florescent substance is excited by the light from the light source 204 and emits the florescence. The intensity of the florescence emitted from the florescent substance is enhanced due to the surface plasmon resonance. Because of having the above-described configuration, the sensor cell 202 can detect the analyte, such as the virus, with high sensitivity.

Although, in FIG. 2, the sensor substrate 202b is disposed on a bottom surface of the flow channel 202a of the sensor cell 202, the sensor substrate may be formed integrally with the flow channel 202a. The sensor substrate 202b is made of resin such as olefin, for example, and has multiple protrusions in the detection region 202c. Part of the multiple protrusions is covered with a metal film, thus forming the metal microscopic structure 2021. A first antibody is immobilized onto the metal microscopic structure 2021. The first antibody is an immobilized antibody capable of specifically binding to the virus, namely the analyte.

In FIG. 3A, the sensor substrate 202b has a rectangular shape in a plan view, and includes the multiple detection regions 202c. However, the shape of the sensor substrate 202b and the number of the detection regions 202c may be determined as appropriate according to design. Details of the metal microscopic structure 2021 will be described later.

The inlet guide 203 introduces the sample and the florescent substance to the sensor cell 202. More specifically, the inlet guide 203 drops the sample liquid 2031 containing both the sample and the florescent substance into the sensor cell 202. The sample liquid 2031 may contain the sample and a second antibody (hereinafter also called a "labeled antibody") labeled with the florescent substance. The second antibody has the property of specifically binding to the virus that has been specifically bound to the first antibody. The sample is a liquid possibly containing the analyte such as the virus. In this embodiment, the sample is the collection liquid into which the fine particles possibly containing the virus are mixed. The sample is discharged from the cyclone 104 and is fed to the detection device 200 via the liquid flow path 111.

When the virus is contained in the sample, the virus is bound to the metal microscopic structure 2021 with the first antibody interposed therebetween. At the same time, the virus is further bound to the second antibody labeled with the florescent substance. In other words, a complex of the first antibody, the virus, the second antibody, and the florescent substance is bound to the metal microscopic structure. When the metal microscopic structure 2021 is irradiated with the light in such a state, the florescence is emitted from the florescent substance bound indirectly to the virus, and the emitted florescence is enhanced by the surface plasmons. In the following, the florescence enhanced by the surface plasmons is called surface-enhanced florescence.

The light source 204 is an example of an irradiation device used to irradiate the detection region 202c with the excitation light. Suitable one of related-art light sources can be optionally utilized as the light source 204 without particular limitations. For example, a laser, such as a semiconductor laser or a gas laser, can be utilized as the light source 204, A light source emitting the excitation light of a wavelength at which the interaction with materials contained in the analyte, such as the virus, is small may be utilized as the light source 204. The wavelength of the excitation light may be in the range of longer than or equal to 400 nm and shorter than or equal to 2000 nm, for example, and may be a wavelength at which the interaction with water or the virus components is small. Alternatively, the wavelength of the excitation light may be a wavelength in the range of longer than or equal to 600 nm and shorter than or equal to 850 nm at which the semiconductor laser can be utilized (for example, 650 nm, 785 nm, or 830 nm).

The beam splitter 205 separates the surface-enhanced florescence emitted from the detection region 202c upon irradiation with the excitation light from the light source 204, More specifically, the beam splitter 205 allows the excitation light from the light source 204 to pass therethrough while separating the surface-enhanced florescence emitted from the detection region 202c and guiding the surface-enhanced florescence to the optical detector 207.

The lens 206 condenses the excitation light, which has been emitted from the light source 204 and has passed through the beam splitter 205, to the detection region 202c, Suitable one of related-art lenses can be optionally utilized as the lens 206 without particular limitations.

The optical detector 207 disperses the surface-enhanced florescence introduced from the beam splitter 205, detects the light in a particular wavelength band, and outputs an electrical signal corresponding to an amount of the virus in the sample.

Suitable one of related-art optical detectors can be optionally utilized as the optical detector 207 without particular limitations insofar as the optical detector can selectively obtain and detect the light in the particular wavelength band. For example, an interference filter transmitting the light in the particular wavelength band therethrough for the dispersion of incident light, a Czerny-Turner spectrometer using a grating for the dispersion of incident light, or an echelle spectrometer can be utilized as the optical detector 207. The optical detector 207 may further include a notch filter capable of removing the excitation light from the light source 204 before the light is introduced to the optical detector 207, or a long-pass filter capable of transmitting the surface-enhanced florescence emitted from the detection region 202c therethrough without transmitting the excitation light from the light source 204 therethrough. For the sake of simplicity, a device for the dispersion of incident light is not illustrated in the optical detector 207.

Configuration of Controller

The controller 300 controls the operation of the entire detection system 10. More specifically, the controller 300 controls the collection device 100 and the detection device 200.

The controller 300 controls, for example, the start of measurement of the virus floating in the air. More specifically, the controller 300 drives the aspirator 101 to suck the atmospheric air around the air inlet 105, and drives the pump 103 to supply the collection liquid in the collection liquid tank 102 to the cyclone 104. At that time, the cyclone 104 is operated with the driving of the aspirator 101. Then, the controller 300 causes the cyclone 104 to mix the fine particles possibly containing the virus in the sucked air with the collection liquid, thereby preparing the sample. Then, the controller 300 causes the cyclone 104 to supply the sample to the detection device 200 via the liquid flow path 111. The controller 300 may operate so as to prepare the sample liquid 2031 by mixing the sample and the florescent substance (or the second antibody labeled with the florescent substance) before the sample reaches the detection device 200. Alternatively, the controller 300 may control the inlet guide 203 to supply the sample liquid 2031 to the sensor device 201, or to successively supply the sample and the florescent substance (or the second antibody labeled with the florescent substance) to the sensor device 201 in the mentioned order. Furthermore, the controller 300 controls the light source 204 to emit the light and to irradiate the detection region 202c with the emitted light, and controls the optical detector 207 to detect the surface-enhanced florescence emitted from the detection region 202c.

For example, the controller 300 may control the pumps under preset conditions in accordance with various input parameters. With that control, the sample liquid 2031 of the predetermined volume is supplied to the sensor device 201 of the detection device 200. Furthermore, the controller 300 may have the timer function, for example, and may generate and store time information required for each operation. In addition, the controller 300 may have the function of obtaining a measurement value from the detection device 200 and calculating the change over time of the concentration of the virus floating in the air on the basis of the measurement value and the time information.

The controller 300 is realized with, for example, one or more dedicated electronic circuits. The one or more dedicated electronic circuits may be integrated on one chip or separately formed on multiple chips. The controller 300 may be realized, instead of the one or more dedicated electronic circuits, with a universal processor (not illustrated) and a memory (not illustrated) storing software programs or instructions. In such a case, the processor functions as the controller 300 with execution of the software programs or the instructions.

Configuration of Metal Microscopic Structure

The detailed configuration of the metal microscopic structure 2021 will be described below with reference to FIGS. 3A-3C.

FIG. 3B is an enlarged sectional view of the metal microscopic structure 2021 taken along a cross-section line 111B-111B in FIG. 3A.

As illustrated in FIG. 3A, the metal microscopic structure 2021 configured to have a nano-scale structured surface and to generate the surface plasmon resonance is formed in the detection region 202*c* of the sensor substrate 202*b*. The metal microscopic structure 2021 is given as a metal-film covered region in the detection region 202*c*, and includes a base member 2022 made of resin, such as olefin, and a metal film 2023.

The base member 2022 includes a nano-structure that is formed on one principal surface (surface on a plus side of the Z-axis) by nanoimprint or injection molding. As illustrated in FIG. 3B, the nano-structure includes multiple protrusions 2022*a*. The protrusions 2022*a* are arrayed at predetermined intervals and, in this embodiment, are arranged in the form of regular triangle lattices in a plan view as shown in FIG. 3C. The regular triangular lattice is also called a hexagonal lattice. The shape of each of the protrusions 2022*a* is not limited to a particular one, and may be a circular columnar shape, for example. In the protrusions 2022*a*, a size ratio of a height t3 to a pitch d3 may be 1:1 to 1:3. In this embodiment, in each of the protrusions 2022*a*, the height t3 is more than or equal to 160 nm and less than or equal to 240 nm, and a thickness (diameter in the case of the circular columnar shape) d1 is more than or equal to 184 nm and less than or equal to 276 nm. An interval (hereinafter called a "gap") d2 between the adjacent protrusions 2022*a* is more than or equal to 184 nm and less than or equal to 276 nm, and the pitch d3 is more than or equal to 368 nm and less than or equal to 552 nm, for example. The nano-structure of the base member 2022 is not limited to the above-described one, and the base member 2022 may include multiple hemispheres instead of the protrusions 2022*a*. The base member 2022 is an example of the base member including the protrusions 2022*a* arrayed at the predetermined intervals. The base member is not limited to a resin-made base member and may be a ceramic base member, for example.

In the present disclosure, the wavelength of the excitation light and the wavelength of the florescence are each longer than or equal to 400 nm and shorter than or equal to 850 nm. The excitation light is the light emitted from the light source 204. The florescence is florescence emitted from the florescent substance and enhanced by the surface plasmons that have been generated from the metal microscopic structure 2021 in the detection region 202*c*, namely by the surface-enhanced florescence, and is detected by the optical detector 207.

In this embodiment, the wavelength of the excitation light and the wavelength of the florescence are each, for example, longer than or equal to 750 nm and shorter than or equal to 850 nm. In such a case, in each of the protrusions, the height t3 is 200 nm, the thickness d1 is 230 nm, the gap d2 is 230 nm, and the pitch d3 is 460 nm, for example. In this embodiment, when the above-mentioned conditions are satisfied, it is possible to generate the surface plasmons with a resonance wavelength in the wavelength band of longer than or equal to 750 nm and shorter than or equal to 850 nm.

The metal film 2023 is formed by coating a metal film on the base member 2022. The metal film 2023 includes a first metal film 2024 formed on the base member 2022, and a second metal film 2025 formed on the first metal film 2024. The second metal film 2025 may be, for example, a metal film with smaller surface roughness than the first metal film 2024. An example of a method of forming the metal film 2023 will be described later in connection with a method of manufacturing the sensor substrate.

The metal film 2023 includes the multiple projections 2023*a* formed corresponding to the multiple protrusions 2022*a* of the base member 2022. When the wavelength of the excitation light and the wavelength of the florescence are each longer than or equal to 750 nm and shorter than or equal to 850 nm, the film thickness of the metal film 2023 is about 400 nm, for example.

The multiple projections are made of the metal film 2023 covering the base member 2022 and are configured to generate the surface plasmons upon irradiation with light. Here, the light used for the irradiation is light of a wavelength capable of exciting a metal material that forms the metal film 2023, namely the excitation light. A film thickness t2 of the metal film 2023 positioned in a bottom portion of a gap between every adjacent two of the projections 2023*a* is greater than the height t3 of the protrusions 2022*a* and is more than or equal to 90% and less than or equal to 100% of a film thickness t1 of the metal film deposited on top portions of the protrusions 2022*a*. Here, the film thickness t1, the film thickness t2, and the height t3 represent lengths in a direction parallel to the Z-axis. The film thickness t1 and the film thickness t2 may be each an average film thickness; and the height t3 may be an average height.

The vertical sectional shape of each of the projections 2023*a* is a forward tapered shape. Here, the wording "vertical sectional shape" implies a shape obtained by cutting the metal microscopic structure 2021 along a plane (ZX-plane) perpendicular to the base member 2022 and looking at the cut cross-section from the direction of the Y-axis. The wording "forward tapered shape" implies such a shape that a cross-sectional area of the projection 2023*a* taken parallel to the surface of the base member 2022 gradually reduces from a base portion toward the top portion of the projection 2023*a*. The base portion of the projection 2023*a* represents a portion positioned at the same height of the bottom portion of the gap between the adjacent projections 2023*a*. The top portion of the projection 2023*a* represents a portion with a maximum height from the base portion of the projection 2023*a*. The shape of each of the projections may be, for example, bowl-shaped, hemispherical, or truncated conical.

Intervals between every adjacent two of the projections are given as follows. When cutting the adjacent projections along a plane that passes the center of each of the projections in a plan view and that is perpendicular to the substrate, an interval d4 between the projections on a top portion side is, for example, more than or equal to 40 nm and less than or equal to 120 nm, and an interval d5 between the projections on a bottom portion side is, for example, more than or equal to 10 nm and less than or equal to 40 nm.

The gap (interval) d5 between every adjacent two of the projections 2023a is a size enough for at least the analyte to pass therethrough and is preferably a size enough for the bound body of the analyte and the luminous body to pass therethrough. The gap d5 is, for example, 100% to 200% of the length of the bound body. The bound body may contain a coupling substance acting to bind the analyte and the luminal body. The coupling substance is a substance with the property of specifically binding to the analyte and may be an antibody, for example.

Figure 4:
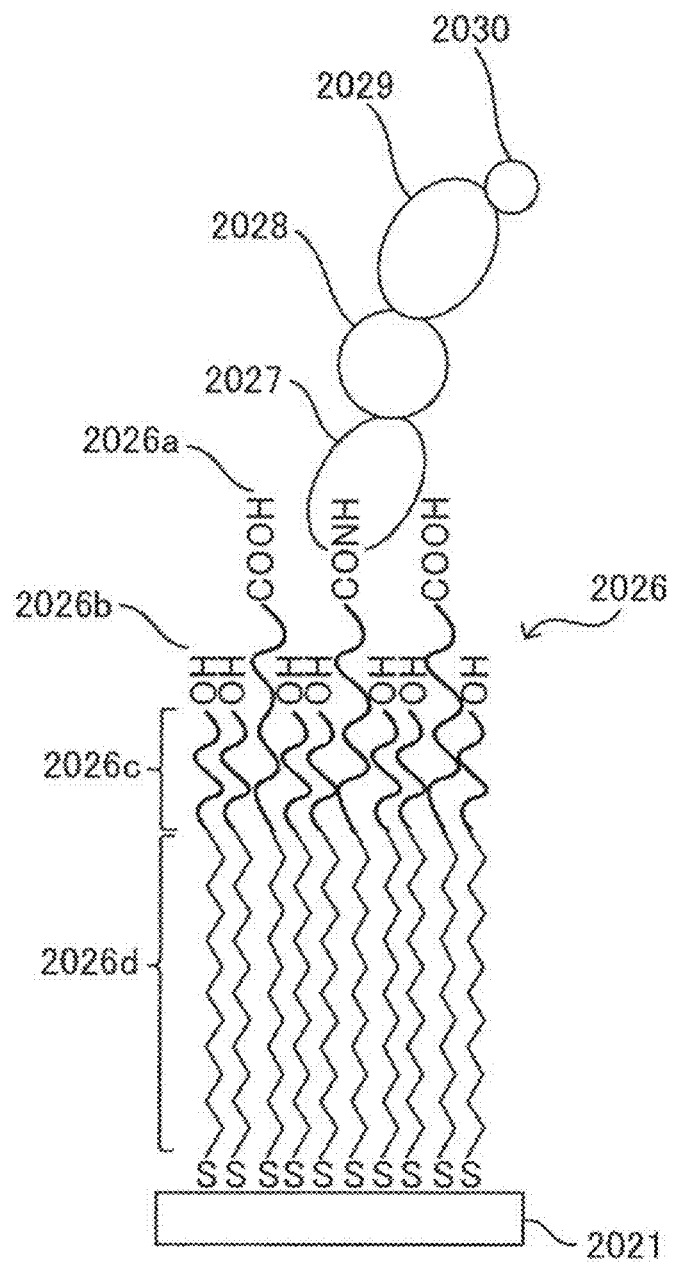
FIG. 4 is an explanatory view illustrating a linker material in the embodiment.

The material of the metal film 2023 needs not to be limited to a particular one and may be gold (Au), silver (Ag), copper (Cu), aluminum (Al), or an alloy containing gold, silver, copper or aluminum as a main component. In this embodiment, the material of the metal film 2023 is gold, Formation of Linker Material A linker material for immobilizing the first antibody onto the metal microscopic structure 2021 will be described below with reference to FIG. 4. FIG. 4 is an explanatory view illustrating the linker material 2026 in the embodiment.

As illustrated in FIG. 4, the surface of the metal microscopic structure 2021 is covered with the linker material 2026. The linker material 2026 is a self-assembled monolayer (hereinafter also called a "SAM") containing a linker molecule 2026a and a non-linker molecule 2026b. A first antibody 2027 is immobilized onto the metal microscopic structure 2021 with the linker molecule 2026a interposed therebetween.

The linker molecule 2026a includes a thiol group at one end and a carboxyl group at the other end. The thiol group is bound to the surface of the metal microscopic structure 2021. The carboxyl group is peptide-bound to the first antibody 2027.

The linker molecule 2026a further includes, between the thiol group and the carboxyl group, an alkyl chain 2026c with the carbon number more than or equal to 10 and a polyethylene glycol (PEG) chain 2026d. More specifically, the alkyl chain 2026c is coupled to the thiol group and the polyethylene glycol chain 2026d, and the polyethylene glycol chain 2026d is coupled to the alkyl chain 2026c and the carboxyl group.

The non-linker molecule 2026b includes a thiol group at one end and a hydroxyl group at the other end. The thiol group is bound to the surface of the metal microscopic structure 2021, The hydroxyl group is hydrophilic and hence suppresses nonspecific adsorption between a second antibody 2029 and a fluorescent substance 2030 (also called a "luminous body").

The non-linker molecule 2026b further includes, between the thiol group and the hydroxyl group, the alkyl chain 2026c with the carbon number more than or equal to 10 and the polyethylene glycol chain 2026d. More specifically, the alkyl chain 2026c is coupled to the thiol group and the polyethylene glycol chain 2026d, and the polyethylene glycol chain 2026d is coupled to the alkyl chain 2026c and the hydroxyl group.

In this embodiment, the number of the linker molecules 2026a included in the linker material 2026 is smaller than the number of the non-linker molecules 2026b.

When a virus (analyte) 2028 is included in the sample liquid 2031, the virus 2028 is bound to the first antibody 2027 immobilized onto the metal microscopic structure 2021. Moreover, the second antibody 2029 labeled with the fluorescent substance 2030 is bound to the virus 2028.

When the metal microscopic structure 2021 is irradiated with the excitation light, fluorescence is emitted from the fluorescent substance 2030, and the fluorescence is enhanced by the surface plasmons generated on the metal microscopic structure 2021. In other words, the surface-enhanced florescence corresponding to an amount of the virus 2028 is emitted.

The first antibody 2027 and the second antibody 2029 are antibodies with the property of specifically binding to the analyte and are, for example, VHH antibodies. The first antibody 2027 and the second antibody 2029 are not limited to VHH antibodies and may be IgG antibodies.

Operation of Detection Device

Figure 5:
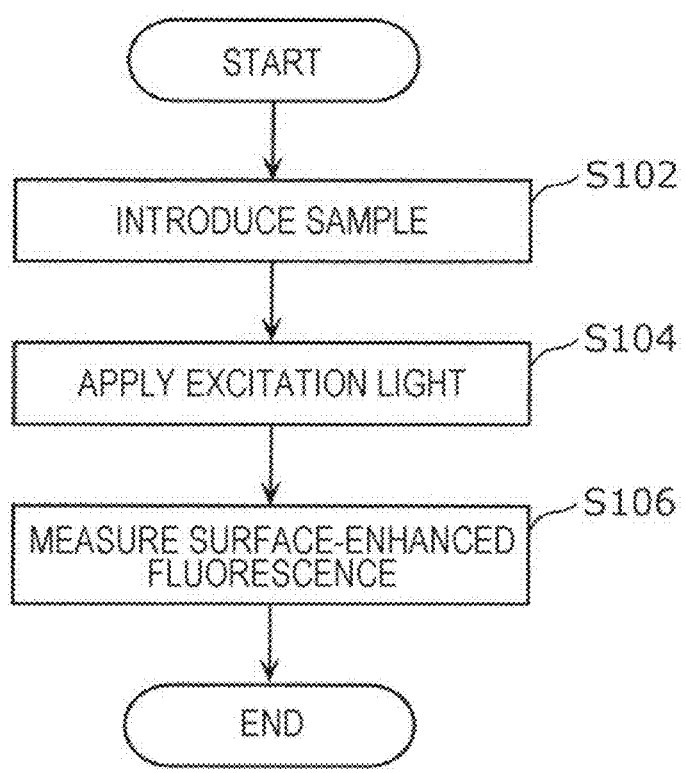
FIG. 5 is a flowchart illustrating an example of a method of detecting an analyte with the sensor substrate in the embodiment.

The operation of the detection device 200 having the above-described configuration will be described below with reference to FIG. 5. FIG. 5 is a flowchart illustrating an example of a method of detecting the analyte with the sensor substrate 202b in the embodiment.

First, the inlet guide 203 introduces, to the sensor cell 202, the sample liquid 2031 (hereinafter also called the "sample") that includes both the fine particles possibly containing the virus and the fluorescent substance (here, the second antibody labeled with the fluorescent substance) (S102). Then, the light source 204 emits the excitation light to the detection region 202c of the sensor cell 202 to which the sample has been introduced (S104). At that time, the metal microscopic structure 2021 and the bound body of the virus and the fluorescent substance are irradiated with the excitation light. Then, the optical detector 207 measures the surface-enhanced florescence, namely the florescence having been emitted from the fluorescent substance upon irradiation with the excitation light and having been enhanced by the surface plasmons, thereby detecting the virus in the sample (S106).

Method of Manufacturing Sensor Substrate

Figure 6:
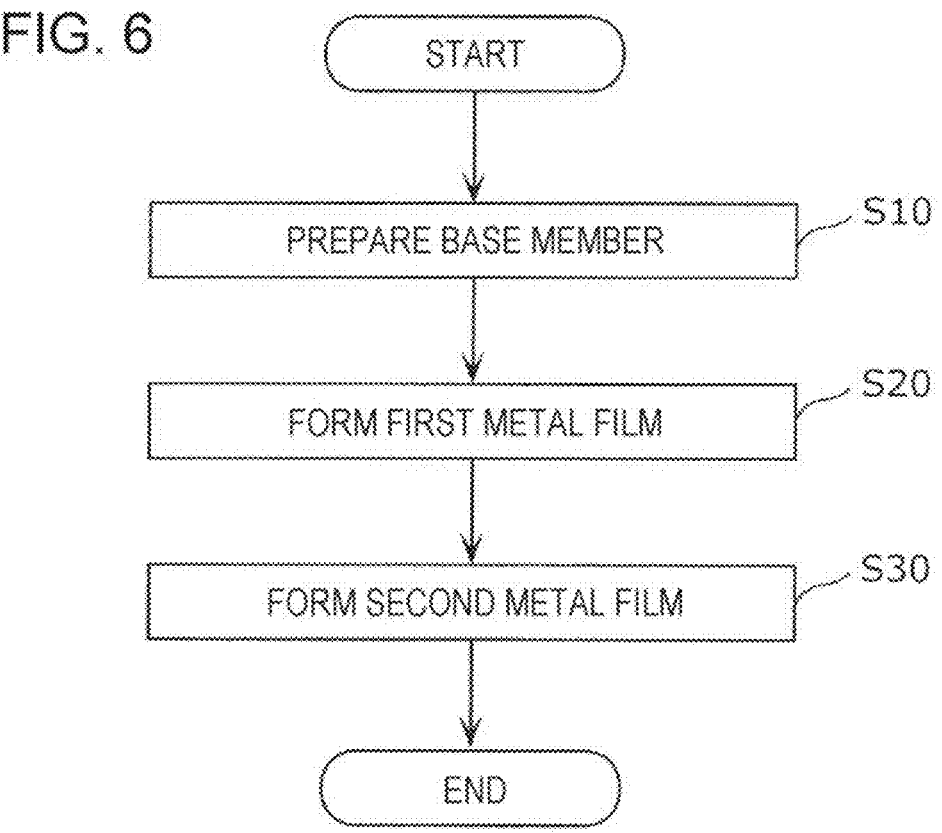
FIG. 6 is a flowchart illustrating an example of a method of manufacturing the sensor substrate in the embodiment.

A method of manufacturing the sensor substrate 202b will be described below with reference to FIG. 6. FIG. 6 is a flowchart illustrating an example of the method of manufacturing the sensor substrate 202b in this embodiment.

First, the base member 2022 including the multiple protrusions 2022a formed on one principal surface at the predetermined intervals is prepared (S10). A method of forming the protrusions 2022a is not limited to a particular one and may be, for example, nanoimprint or injection molding. The protrusions 2022a may be formed on the entirety of the one principal surface of the base member 2022 or formed only at a location corresponding to the detection region 202c (see FIG. 3A).

Then, a first metal film 2024 is formed on the base member 2022 (S20). More specifically, the first metal film 2024 is formed at the location corresponding to the detection region 202c after patterning. A method of forming the first metal film 2024 is just required to satisfy the condition that the metal material is deposited in a larger amount in the direction perpendicular to the plane of the base member 2022 (in the Z-axis direction in FIG. 3B) than as compared with a method of forming the second metal film 2025 in a subsequent step S30. Namely, the method of forming the first metal film 2024 is not limited to a particular one and may be, for example, vapor deposition. The vapor deposition may be, for example, electron beam (EB) vapor deposition, resistance heating vapor deposition, radio-frequency induction vapor deposition, or laser vapor deposition. Among those examples, the EB vapor deposition or the resistance heating vapor deposition may be used from the viewpoint of improving the universality of the manufacturing method because those vapor deposition methods are more generally used. In this embodiment, the first metal film 2024 is formed by the EB vapor deposition. Thus, in this step S20, the first metal film 2024 is formed in a uniform thickness in the plane of the base member 2022.

Then, the second metal film 2025 is formed on the first metal film 2024 (S30). A method of forming the second metal film 2025 is just required to satisfy the condition that the metal material is deposited in a larger amount in the horizontal direction (in the Y-axis direction in FIG. 3B) than as compared with the method of forming the first metal film 2024. Namely, the method of forming the second metal film 2025 is not limited to a particular one and may be, for example, sputtering. The sputtering may be, for example, DC (direct current) sputtering, RF (radio frequency) sputtering, DC magnetron sputtering, RF magnetron sputtering, or ion beam sputtering. Among those examples, the DC sputtering or the RF sputtering may be used from the viewpoint of improving the universality of the manufacturing method because those sputtering methods are more generally used. Since the second metal film 2025 is formed by the sputtering, irregularities in the surface of the first metal film 2024 can be absorbed by the second metal film 2025. As a result, the metal film 2023 with a smooth surface can be obtained.

Then, although not illustrated, the metal microscopic structure 2021 obtained through the above-described steps S10 to S30 is coated with the linker material 2026. For example, a SAM (Self-Assembled Monolayer) is formed only on the surface of the metal film 2023 by dipping the sensor substrate 202b (see FIG. 3A) into a SAM solution.

Then, the first antibody 2027 is immobilized to the metal film 2023 with the linker material 2026 interposed therebetween. For example, the VHH antibody is peptide-bound to the SAM. The first antibody 2027 is thereby immobilized onto the metal microscopic structure 2021. On that occasion, no antibodies are immobilized to a region in which the metal film 2023 is not formed, because the SAM is not formed in such a region. In the step S30, the second metal film 2025 may be formed such that a film thickness of the second metal film 2025 (maximum value of thickness in the Z-axis direction) is thinner than a film thickness of the first metal film 2024 (maximum value of thickness in the Z-axis direction). In that case, the surface smoothness of the metal microscopic structure 2021 can be increased while the uniformity of thickness of the first metal film 2024, formed by the electron beam vapor deposition, in the plane of the sensor substrate 202b is maintained. Accordingly, a plasmon characteristic is stabilized in the substrate plane, and the sensor substrate 202b having high performance of light enhancement and being able to reduce nonspecific adsorption is obtained. Thus, in the sensor device 201 using the sensor substrate 202b, a noise signal can be reduced due to reduction of the nonspecific adsorption, and faint light emission can be detected due to the high performance of light enhancement. As a result, a high S/N can be ensured and the detection sensitivity can be increased.

Advantageous Effects and Others

As described above, the metal microscopic structure 2021 according to this embodiment includes the base member 2022 including the multiple protrusions 2022a arrayed at the predetermined intervals, and the multiple projections 2023a are made of the metal film 2023 covering the base member 2022 and configured to generate the surface plasmons upon irradiation with light. The film thickness t2 of the metal film 2023 positioned in the bottom portion of the gap between every adjacent two of the projections 2023a is greater than the height t3 of the protrusions 2022a and is more than or equal to 90% and less than or equal to 100% of the film thickness t1 of the metal film 2023 deposited on the top portions of the protrusions 2022a.

In the metal microscopic structure 2021, since the film thickness t2 of the metal film 2023 positioned in the bottom portion of the gap between every adjacent two of the projections 2023a is greater than the height t3 of the protrusions 2022a, the protrusions 2022a are completely covered with the metal film 2023. In addition, a sufficient thickness is ensured as the film thickness t2 of the metal film 2023 positioned in the bottom portion of the above-mentioned gap. Accordingly, the metal microscopic structure 2021 is less susceptible to the influence of the base member 2022 at the location where the film thickness is most likely to become thin. As a result, even when the multiple detection regions 202c are discretely arranged as illustrated in FIG. 3A, for example, the metal microscopic structure 2021 can exhibit a stable optical electric-field enhancement effect, namely a stable plasmon characteristic, in all of the detection regions 202c in the plane of the sensor substrate 202b.

Furthermore, in the metal microscopic structure 2021, the film thickness t1 of the metal film 2023 deposited on the top portions of the protrusions 2022a is thicker than the film thickness of the metal film 2023 positioned in the bottom portion of the gap between every adjacent two of the projections 2023a, the relevant gap has a larger depth. The larger depth of the gap increases a region where the surface plasmons are generated. Moreover, the larger depth of the gap can hold a larger number of the bound bodies each being a combination of the analyte and the luminous body to stay in the region where the surface plasmons are generated. In addition, the larger depth of the gap makes it easier to design a width of the gap to the desired size. For example, the metal microscopic structure 2021 may be designed such that a proportion of regions where the width of the gap is small increases, or such that the width of the gap is minimized in the bottom portion of the gap.

Because of having the above-described features, the metal microscopic structure 2021 according to this embodiment can detect a low-concentration analyte with high sensitivity.

In the metal microscopic structure 2021 according to this embodiment, the vertical sectional shape of each of the multiple projections 2023a is a forward tapered shape.

In the above case, since the gap between every adjacent two of the projections 2023a is wider on the top portion side of the projections 2023a, the bound body of the analyte and the luminous body is more likely to enter the gap. Therefore, a proportion of the bound body entering the gap can be increased. Furthermore, the gap between every adjacent two of the projections 2023a gradually narrows toward the bottom portion of the gap. For example, when the width of the gap is minimized in the bottom portion of the gap, the optical electric-field enhancement effect is maximized in the bottom portion of the gap. Since the gap gradually narrows toward the bottom portion of the gap, the bound body is more likely to reach the bottom portion of the gap, and a larger number of the bound bodies are more likely to be held in the bottom portion of the gap. In other words, a larger number of the bound bodies can be held in the region where the optical electric-field enhancement effect is maximized. As a result, the metal microscopic structure 2021 according to this embodiment can detect the low-concentration analyte with higher sensitivity.

In the metal microscopic structure 2021 according to this embodiment, the base member 2022 is made of resin, each of the protrusions 2022a has a circular columnar shape, the protrusions 2022a are arranged in the form of regular triangle lattices in a plan view, the thickness d1 (see FIG. 3B) of the protrusions 2022a is more than or equal to 184 nm and less than or equal to 276 nm, and the interval d2 (see FIG. 3B) between every adjacent two of the protrusions 2022a is more than or equal to 184 nm and less than or equal to 276 nm.

Since the base member 2022 is made of resin as described above, the protrusions 2022a can easily be formed in the desired shape and at the desired interval. Furthermore, since the protrusions 2022a have the circular columnar shape and are arranged in the form of regular triangle lattices in a plan view, the multiple projections 2023a with a uniform lattice period can be formed when the protrusions 2022a are covered with the metal film 2023. In addition, since the thickness d1 of the protrusions 2022a and the interval d2 between every adjacent two of the protrusions 2022a are each in the above-mentioned range, the metal microscopic structure 2021 uniform in the substrate plane of the sensor substrate 202b can be obtained when the protrusions 2022a are covered with the metal film 2023.

In the metal microscopic structure 2021 according to this embodiment, the height t3 (see FIG. 3B) of each of the protrusions 2022a may be more than or equal to 160 nm and less than or equal to 240 nm, and the film thickness t2 (see FIG. 3B) of the metal film 2023 positioned in the bottom portion of the gap between every adjacent two of the projections 2023a may be more than or equal to 200 nm and less than or equal to 600 nm.

In the above case, since the film thickness t2 of the metal film 2023 positioned in the bottom portion of the gap between every adjacent two of the projections 2023a is greater than the height t3 of each of the protrusions 2022a, the protrusions 2022a are completely covered with the metal film 2023. In addition, a sufficient thickness is ensured as the film thickness t2 of the metal film 2023 positioned in the bottom portion of the above-mentioned gap. Accordingly, the metal microscopic structure 2021 is less susceptible to the influence of the base member 2022 at the location where the film thickness is most likely to become thin, and can exhibit the stable optical electric-field enhancement effect, namely the stable plasmon characteristic.

Figure 3B:
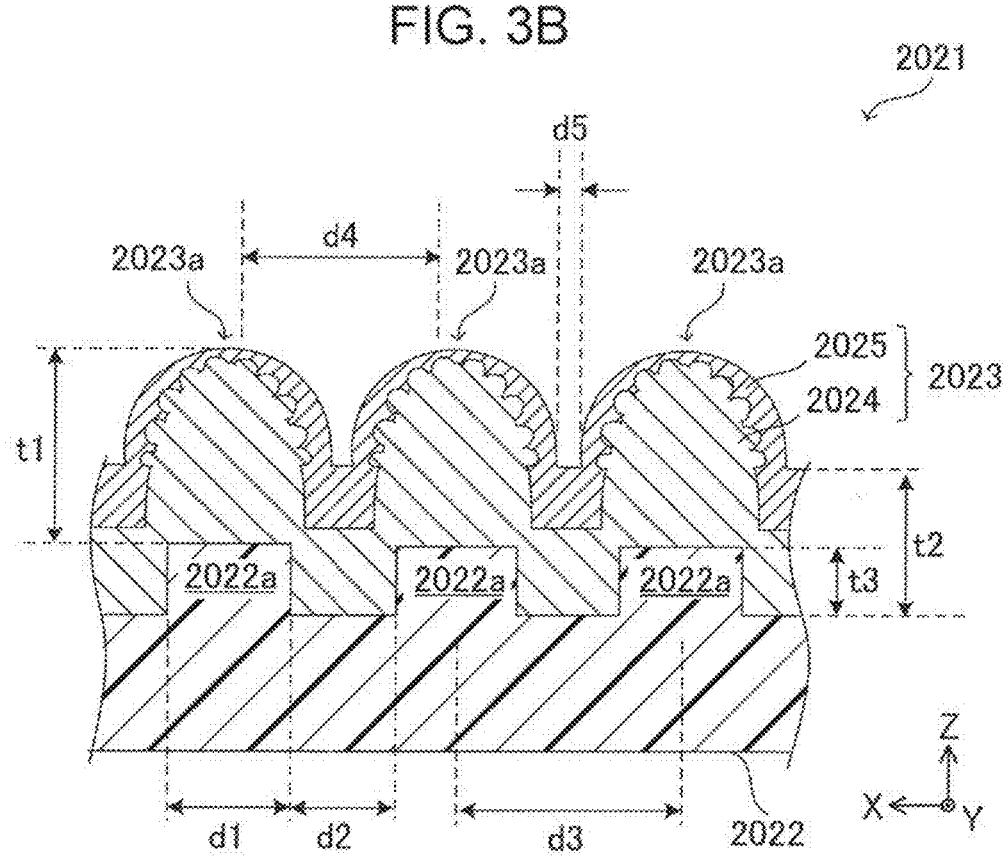
FIG. 3B is an enlarged sectional view illustrating an example of a metal microscopic structure according to the embodiment.
Figure 3C:
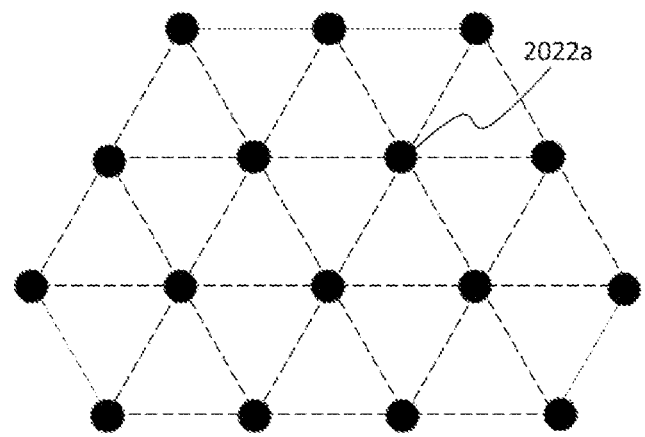
FIG. 3C is a schematic plan view illustrating an example of a metal microscopic structure according to the embodiment.

In the metal microscopic structure 2021 according to this embodiment, in a cross section (ZX-plane in FIG. 3B) that passes the center of each of the projections 2023a in a plan view and that is perpendicular to the base member 2022, an interval between every adjacent two of the projections 2023a is more than or equal to 40 nm and less than or equal to 120 nm on the top portion side of the projections 2023a (plus side of the Z-axis in FIG. 3B) and is more than or equal to 10 nm and less than or equal to 40 nm on the bottom portion side of the projections 2023a (minus side of the Z-axis in FIG. 3B).

In the above case, since the gap between every adjacent two of the projections 2023a is wider on the top portion side of the projections 2023a, the bound body of the analyte and the luminous body is more likely to enter the gap. Therefore, a proportion of the bound body entering the gap can be increased. Furthermore, the gap between every adjacent two of the projections 2023a gradually narrows toward the bottom portion side of the projections 2023a, namely the bottom portion side of the gap. For example, when the width of the gap is minimized in the bottom portion of the gap, the optical electric-field enhancement effect is maximized in the bottom portion of the gap. Since the gap gradually narrows toward the bottom portion side of the gap, the bound body is more likely to reach the bottom portion of the gap, and a larger number of the bound bodies are more likely to be held in the bottom portion of the gap. In other words, a larger number of the bound bodies can be held in the region where the optical electric-field enhancement effect is maximized. For example, when a bound body is formed by binding the analyte and a labeled antibody that is obtained by modifying an antibody with a fluorescent substance, the antibody specifically binding to the analyte, the bound body has a length of smaller than 10 nm. Even in such a case, since the above-mentioned gap is more than or equal to 10 nm on the bottom portion side of the projections 2023a, it is also possible to hold a larger number of the bound bodies in the bottom portion of the gap, namely in the region where the optical electric-field enhancement effect is maximized. Moreover, the above-mentioned gap is preferably less than or equal to 40 nm on the bottom portion side of the projections 2023a from the viewpoint of increasing the optical electric-field enhancement effect based on the surface plasmons. Thus, the metal microscopic structure 2021 according to this embodiment can detect the low-concentration analyte with higher sensitivity.

In the metal microscopic structure 2021 according to this embodiment, the metal film 2023 is made of gold, silver, copper, aluminum, or an alloy containing gold, silver, copper, or aluminum as a main component.

In the above case, the resonance wavelength of the surface plasmon resonance can be controlled to a wavelength in the desired wavelength range. More specifically, in consideration of that the resonance wavelength of the surface plasmon resonance is different depending on the type of metal, the metal film 2023 can be formed by selecting the desired one from among the above-mentioned materials of the metal film 2023 in match with the fluorescent wavelength of the luminous body (for example, the fluorescent substance) that is used to detect the analyte.

The detection device 200 according to this embodiment includes the metal microscopic structure 2021, the inlet guide 203 configured to introduce both the sample possibly containing the analyte and the luminous body to the metal microscopic structure 2021, the light source 204 capable of emitting light with which the metal microscopic structure 2021 and the bound body of the analyte and the luminous body are irradiated, and the optical detector 207 configured to detect light emitted from the luminous body that has been excited by the light emitted from the light source 204.

With the above-described feature, the detection device 200 introduces the bound body of the analyte and the luminous body to the metal microscopic structure 2021, irradiates the metal microscopic structure 2021 and the bound body having been introduced to the metal microscopic structure 2021 with light, and detects light emitted from the luminous body that has been excited by the light for the irradiation. Therefore, the detection device 200 according to this embodiment can detect and quantitate the analyte by detecting the light emitted from the luminous body.

The detection device 200 according to this embodiment may further include the first antibody 2027 that has the property of specifically binding to the analyte 2028, namely the virus or the virus component, that has been immobilized onto the metal microscopic structure 2021, and the second antibody 2029 that has the property of specifically binding to the analyte 2028 specifically bound to the first antibody 2027 and that has been labeled with the luminous body (for example, the fluorescent substance 2030).

In the above case, since the analyte 2028 specifically binds to the first antibody 2027 that has been immobilized onto the metal microscopic structure 2021, the analyte 2028 can be held on the metal microscopic structure 2021 with the first antibody 2027 interposed therebetween. Accordingly, the analyte 2028 can be more reliably held on the metal microscopic structure 2021. In addition, since the second antibody 2029 labeled with the fluorescent substance 2030, for example, specifically binds to the analyte 2028, the fluorescent substance 2030 can be bound to the analyte 2028, which has been held on the metal microscopic structure 2021, with the second antibody 2029 interposed therebetween. This enables the fluorescent substance 2030 to be more reliably bound to the analyte 2028. As a result, the detection device 200 according to this embodiment can detect the analyte 2028, namely the virus or the virus component, with high sensitivity.

In the detection device 200 according to this embodiment, the wavelength of the light emitted from the light source 204 may be longer than or equal to 400 nm and shorter than or equal to 850 nm, and the wavelength of the light detected by the optical detector 207 may be longer than or equal to 400 nm and shorter than or equal to 850 nm.

In the above case, when the luminous body is the fluorescent substance, for example, it is possible to use the fluorescent substance 2030 satisfying the conditions that the wavelength of the light absorbed by the fluorescent substance 2030 is in the range of longer than or equal to 400 nm and shorter than or equal to 850 nm, and that the wavelength of the fluorescence emitted from the fluorescent substance 2030 is in the range of longer than or equal to 400 nm and shorter than or equal to 850 nm. Accordingly, the detection sensitivity can be increased by suppressing the emission of autofluorescence from a substance, for example; a VHH antibody; contained in the analyte 2028. Hence the above-described feature enables a small amount of the analyte 2028 to be detected with high sensitivity.

EXAMPLES

The present disclosure will be described in more detail below with reference to Examples, but the following Examples are not purported to limit the present disclosure.

In Examples and Comparative Examples described below, the base member was prepared as a resin substrate including a nano-structure with multiple pillars (circular columnar protrusions), the nano-structure being formed on one principal surface of the resin substrate by nanoimprint. The pillar height was 200 nm, the pillar diameter was 230 nm, and the pillar pitch was 460 nm.

Example 1

Figure 7A:
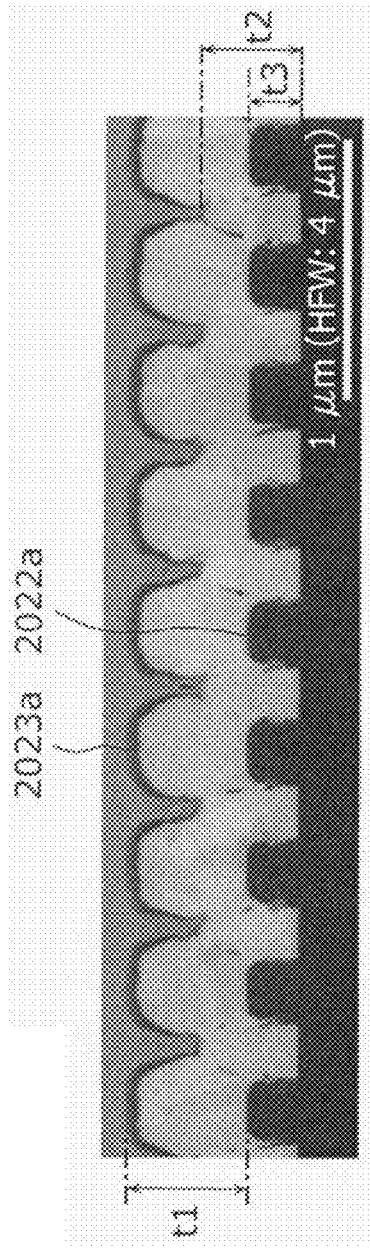
FIG. 7A represents a sectional SEM (Scanning Electron Microscope) image of a metal microscopic structure according to Example 1.

A gold film was formed in a thickness of 300 nm on the above-mentioned resin substrate by the electron beam vapor deposition, and another gold film was then formed in a thickness of 100 nm by the sputtering. FIG. 7A represents a sectional SEM image of the metal microscopic structure obtained in this Example.

Example 2

A gold film was formed in a thickness of 300 nm on the above-mentioned resin substrate by the electron beam vapor deposition, and another gold film was then formed in a thickness of 300 nm by the sputtering. A sectional SEM image of the metal microscopic structure obtained in this Example was similar to that represented in FIG. 7A. Hence the sectional SEM image in this Example is omitted.

The sensor substrate included the metal microscopic structure described above. A SAM was formed on the metal microscopic structure by dipping the sensor substrate into a SAM solution in an incubator at 40° C.

The SAM solution was prepared through the following procedures. First, Carboxy-EG6-undecanethiol and Hydroxy-EG3-undecanethiol were mixed after diluting each of them into a solution of 1 mM ($10^{-3}$ mol/L) with ethanol. Then, the SAM solution was obtained by diluting the mixture 5 times with ethanol.

Thereafter, a terminal carboxyl group of the SAM and a terminal amino group of the first antibody (hereinafter called the "first VHH antibody") were peptide-bound by the EDC (ethyl(dimethylaminopropyl)carbodiimide)-NHS (N-hydroxysuccinimide) reaction, whereby the first VHH antibody was immobilized to the SAM.

Through the above-described procedures, the sensor substrate including the first VHH antibody immobilized to the surface of the metal film of the metal microscopic structure 2021 according to Example 2 was obtained.

Figure 8A:
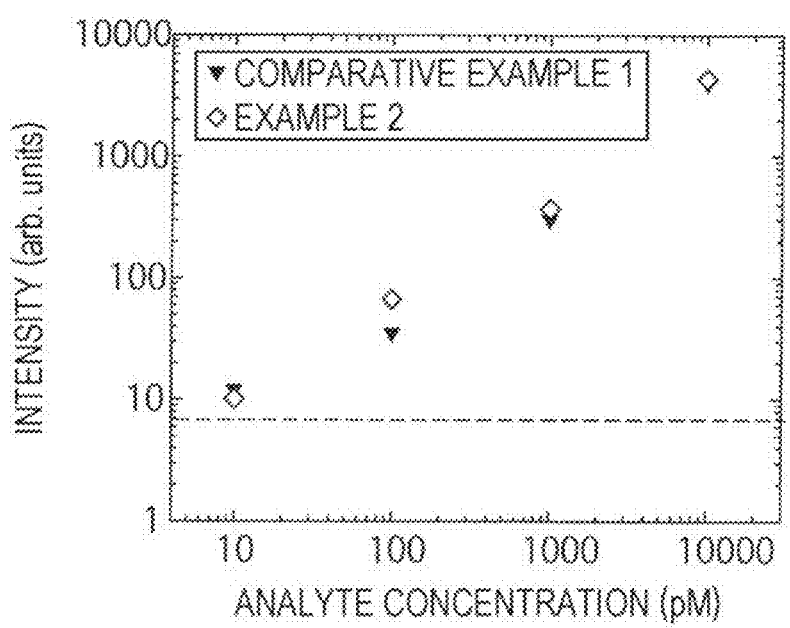
FIG. 8A is a plot representing sensor sensitivity for each of sensor substrates according to Example 2 and Comparative Example 1.

A sample liquid prepared by mixing NP (Nucleoprotein) of an influenza virus, namely an analyte, and the second antibody (hereinafter called the "second VHH antibody") labeled with an organic fluorescent dye (emission wavelength: 800 nm), namely the fluorescent substance, was introduced to the sensor substrate obtained as described above. In other words, a sandwich Assay was performed by binding the NP, namely the analyte, to the first VHH antibody immobilized onto the metal microscopic structure, and by further binding the second VHH antibody labeled with the fluorescent substance to the NP. A complex (first VHH antibody/NP/second VHH antibody labeled with the fluorescent substance) formed by the sandwich Assay was irradiated with a laser beam of 785 nm to excite the organic fluorescent dye, and the intensity of fluorescence emitted from the fluorescent substance and having the wavelength of 800 nm was measured. FIG. 8A represents the measurement result.

Comparative Example 1

Figure 7B:
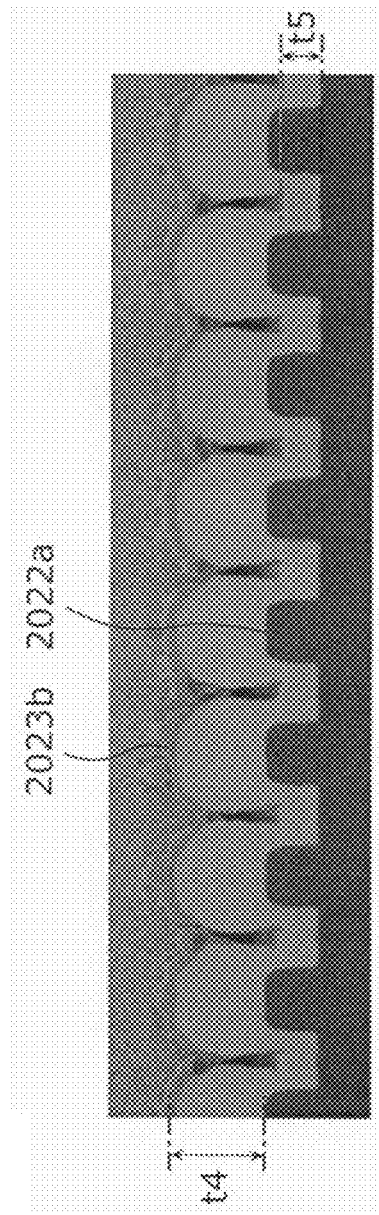
FIG. 7B represents a sectional SEM image of a metal microscopic structure according to Comparative Example 1.

A sensor substrate according to Comparative Example 1 was prepared in the same manner as in Example 1 and Example 2 except for including a metal microscopic structure having a metal film that was formed only by the sputtering, and the sandwich Assay was also performed in the same manner as in Example 2. More specifically, a gold film was formed in a thickness of 400 nm on the above-described resin substrate by the sputtering. FIG. 7B represents a sectional SEM image of the obtained metal microscopic structure. FIG. 8A represents the sensor sensitivity of the sensor substrate according to Comparative Example 1, namely the result of measuring the intensity of the fluorescence emitted from the fluorescent substance.

Comparative Example 2

Figure 7C:
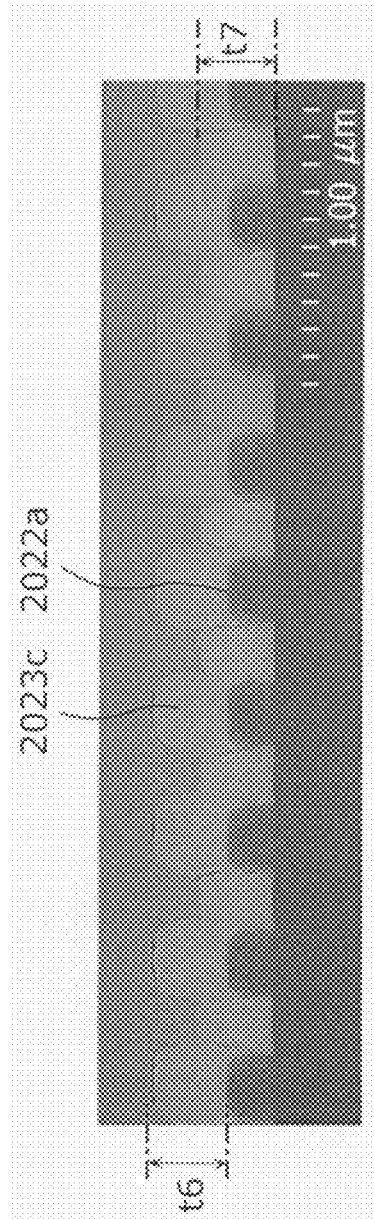
FIG. 7C represents a sectional SEM image of a metal microscopic structure according to Comparative Example 2.
Figure 8B:
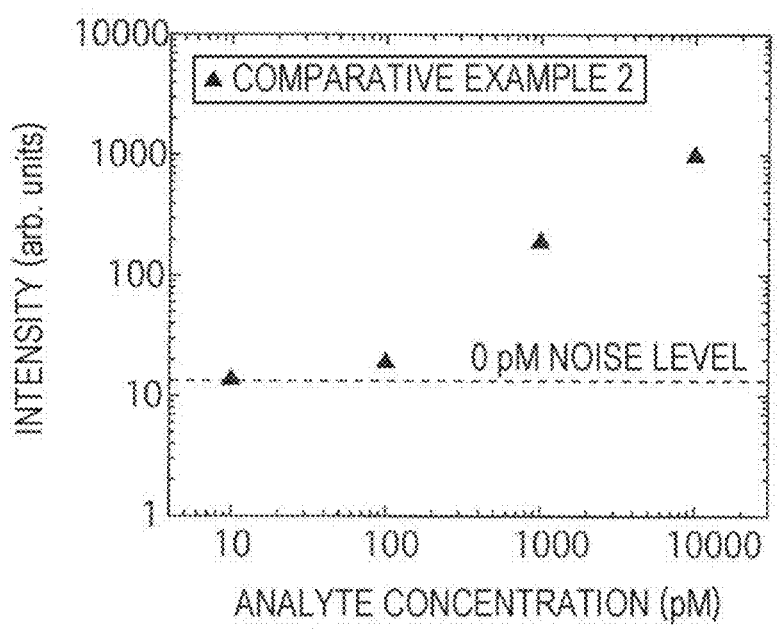
FIG. 8B is a plot representing sensor sensitivity of a sensor substrate according to Comparative Example 2.

A sensor substrate according to Comparative Example 2 was prepared in the same manner as in Example 1 and Example 2 except for including a metal microscopic structure having a metal film that was formed only by the electron beam (EB) vapor deposition, and the sandwich Assay was also performed in the same manner as in Example 2. More specifically, a gold film was formed in a thickness of 300 nm on the above-described resin substrate by the electron beam vapor deposition. FIG. 7C represents a sectional SEM image of the obtained metal microscopic structure. FIG. 8B represents the sensor sensitivity of the sensor substrate according to Comparative Example 2, namely the result of measuring the intensity of the fluorescence emitted from the fluorescent substance.

Results

The sectional configurations of the metal microscopic structures according to Example 1, Comparative Example 1, and Comparative Example 2 will be described below with reference to FIGS. 7A to 7C. In FIGS. 7A to 7C, the heights of the multiple protrusions 2022a on the resin substrate are all the same and are denoted by t3.

FIG. 7A represents the sectional SEM image of the metal microscopic structure according to Example 1. As illustrated in FIG. 7A, the film thickness t2 of the metal film positioned in the bottom portion of the gap between every adjacent two of the projections 2023a was greater than the height t3 of the protrusions 2022a on the resin substrate. Furthermore, the film thickness t2 was more than or equal to 90% and less than or equal to 100% of the film thickness t1 of the metal film deposited on the top portions of the protrusions 2022a.

Although not illustrated, regarding the sectional configuration of the metal microscopic structure according to Example 2, as in Example 1, the film thickness of the metal film positioned in the bottom portion of the gap between every adjacent two of the projections was greater than the height t3 of the protrusions 2022a on the resin substrate and was more than or equal to 90% and less than or equal to 100% of the film thickness of the metal film deposited on the top portions of the protrusions 2022a.

FIG. 7B represents the sectional SEM image of the metal microscopic structure according to Comparative Example 1. As illustrated in FIG. 7B, a film thickness t5 of the metal film positioned in a bottom portion of a gap between every adjacent two of multiple projections 2023b was smaller than the height t3 of the protrusions 2022a on the resin substrate. Moreover, the film thickness t5 was less than or equal to 50% of a film thickness t4 of the metal film deposited on the top portions of the protrusions 2022a.

FIG. 7C represents the sectional SEM image of the metal microscopic structure according to Comparative Example 2. As illustrated in FIG. 7C, a film thickness t7 of the metal film positioned in a bottom portion of a gap between every adjacent two of multiple projections 2023c was greater than the height t3 of the protrusions 2022a on the resin substrate. Moreover, the film thickness t7 was greater than a film thickness t6 of the metal film deposited on the top portions of the protrusions 2022a.

The sensor sensitivities of the sensor substrates according to Example 2, Comparative Example 1, and Comparative Example 2 will be described below with reference to FIGS. 8A and 8B.

FIG. 8A represents the sensor sensitivities of the sensor substrates according to Example 2 and Comparative Example 1. FIG. 8B represents the sensor sensitivity of the sensor substrate according to Comparative Example 2, The nucleoprotein (NP) of the influenza virus was used as the analyte. The NP concentrations were 0 pM, 10 pM, 100 pM, 1000 pM, and 10000 pM.

As seen from FIGS. 8A and 8B, the sensor substrate according to Comparative Example 2 had a high noise level and exhibited low detection intensity with respect to the NP concentrations. On the other hand, the sensor substrate according to each of Example 2 and Comparative Example 1 had a low noise level and exhibited a linear response in detection intensity with respect to the NP concentrations. Comparing the detection intensities at the same NP concentration in the sensor substrates according to Example 2 and Comparative Example 1, however, the detection intensity was higher in the sensor substrate according to Example 2, As described above, the following points were confirmed. According to Example 1 and Example 2, the metal microscopic structure can be obtained in which the film thickness t2 of the metal film positioned in the bottom portion of the above-mentioned gap is greater than the height t3 of the protrusions 2022a and the film thickness t2 is more than or equal to 90% and less than or equal to 100% of the film thickness t1 of the metal film deposited on the top portions of the protrusions 2022a. Furthermore, the sensor substrate including the metal microscopic structure according to Example 2 has good detection sensitivity. Thus the metal microscopic structure can detect the low-concentration analyte with high sensitivity by satisfying the conditions that the film thickness t2 of the metal film positioned in the bottom portion of the gap between every adjacent two of the projections 2023a is greater than the height t3 of the protrusions 2022a on the resin substrate and is more than or equal to 90% and less than or equal to 100% of the film thickness t1 of the metal film deposited on the top portions of the protrusions 2022a.

OTHER EMBODIMENTS

The metal microscopic structure and the detection device according to one or more aspects of the present disclosure have been described above, but the present disclosure is not limited to the above embodiments. Modifications obtained by various modifying the above embodiments based on ideas conceivable by those skilled in the art may also fall within the scope of the one or more aspects of the present disclosure insofar as those modifications do not depart from the gist of the present disclosure.

For example, while the above embodiments have been described in connection with the case in which the sensor substrate including the metal microscopic structure is used in the measurement method utilizing the fluorescence enhancement effect due to the localized surface plasmon resonance, the relevant sensor substrate may be further applied to a measurement method utilizing a refractive index shift of a localized surface-plasmon resonance spectrum.

Figure 9:
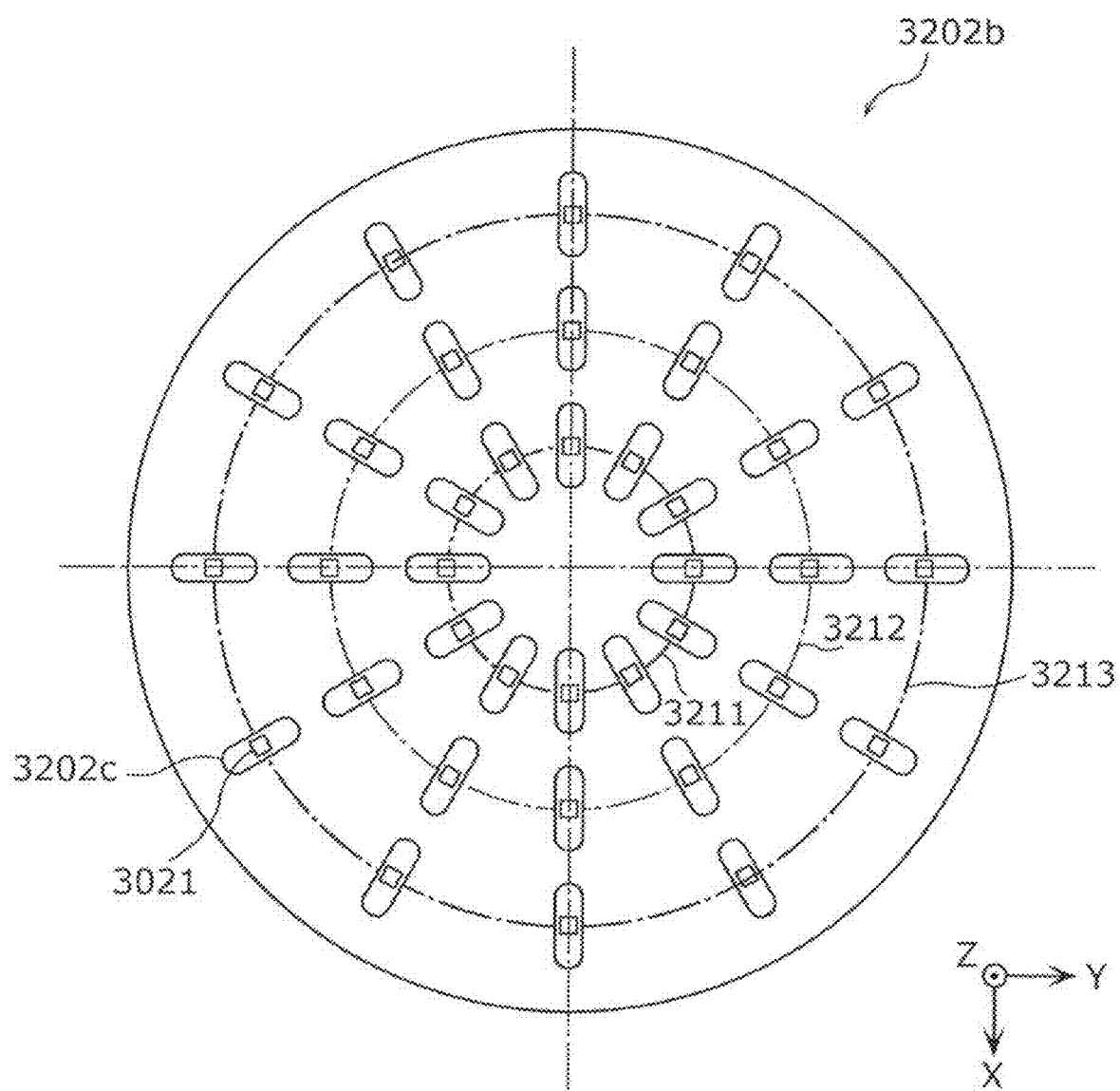
FIG. 9 is a schematic plan view illustrating an example of a sensor substrate according to another embodiment.

While the above embodiments have been described in connection with the case in which the shape of the sensor substrate is rectangular in a plan view, the present disclosure is not limited to that case. For example, the substrate may have a disk shape like a sensor substrate 3202b illustrated in FIG. 9, FIG. 9 is a schematic plan view illustrating an example of the sensor substrate 3202b according to another embodiment. The sensor substrate 3202b may have multiple detection regions 3202c arranged in the circumferential direction of the sensor substrate 3202b along each of circles 3211 to 3213, and the detection regions 3202c may include metal microscopic structures 3021 in a one-to-one relation. Alternatively, the sensor substrate may have a polygonal shape.

While, in the above embodiments, the immobilized antibody is immobilized to the metal film with the linker molecule 2026a interposed therebetween, the immobilized antibody may be immobilized directly to the metal film. For example, the immobilized antibody may be immobilized to the metal film by chemical bonding such as a peptide bond, or by physical adsorption based on an intermolecular force, for example.

While the above embodiments have been described in connection with the case in which film forming conditions are not changed during the film formation processes using the vapor deposition and the sputtering, the present disclosure is not limited to that case.

The present disclosure further includes not only modifications that are obtained by variously modifying the above embodiments based on ideas conceivable by those skilled in the art, but also modifications that are realized by optionally combining the constituent elements and the functions in the above embodiments within the scope not departing from the gist of the present disclosure.

The invention derived from the foregoing present disclosure is as follows.

(Item 1)

A metal microscopic structure comprising:
a base member including multiple protrusions including a first protrusion and a second protrusion; and
a metal film covering the base member,
wherein
in a cross section of the metal microscopic structure, the metal film comprises (desirably, is composed of):
a first projection positioned on a surface of the first protrusion;
a second projection positioned on a surface of the second protrusion; and
a flat portion positioned between the first projection and the second projection (desirably, a rear surface of the flat portion is in contact with a surface of a recess formed on the base member),
the metal film includes multiple projections including the first projection and the second projection,
surface plasmons are generated upon irradiation of (a surface of) the metal film with light,
the flat portion is thicker than the first protrusion and the second protrusion, and
the following mathematical formula (1) is satisfied:

$$0.9 \leq t2/t1 \leq 1.0 \tag{1}$$

where
t1 denotes a height of the first projection, and
t2 denotes a height of the flat portion.

The present disclosure can be applied to a sensor substrate utilizing, for example, emission-enhanced fluorescence and so on. When the present disclosure is applied to a virus sensor, for example, the present disclosure can be used in a sensor substrate to measure the concentration of the virus floating in the air inside a room with high sensitivity for the purpose of reducing the infection risk of the virus to persons in the room.

What is claimed is:

1. A metal microscopic structure comprising:
a base member including multiple protrusions arrayed at predetermined intervals; and
multiple projections made of a metal film covering the base member and configured to generate surface plasmons upon irradiation with light, wherein:
a film thickness of the metal film positioned in a bottom portion of a gap between every adjacent two of the multiple projections is greater than a height of the multiple protrusions and is more than or equal to 90% and less than or equal to 100% of a film thickness of the metal film deposited on top portions of the multiple protrusions,
the metal film includes a first metal film in contact with the multiple projections and a second metal film disposed on the first metal film,
a thickness of the second metal film is smaller than a thickness of the first metal film on top portions of the multiple protrusions,
the base member is made of resin,
each of the multiple protrusions has a circular columnar shape,
the multiple protrusions are arranged in a form of regular triangle lattices in a plan view,
a thickness of the multiple protrusions is more than or equal to 184 nm and less than or equal to 276 nm, and
an interval between every adjacent two of the multiple protrusions is more than or equal to 184 nm and less than or equal to 276 nm.

2. The metal microscopic structure according to claim 1, wherein a vertical sectional shape of each of the multiple projections is a forward tapered shape.

3. The metal microscopic structure according to claim 1, wherein the height of each of the multiple protrusions is more than or equal to 160 nm and less than or equal to 240 nm, and
the film thickness of the metal film positioned in the bottom portion of the gap between every adjacent two of the multiple projections is more than or equal to 200 nm and less than or equal to 600 nm.

4. The metal microscopic structure according to claim 1, wherein an interval between every adjacent two of the multiple projections is more than or equal to 40 nm and less than or equal to 120 nm on a top portion side of the multiple projections in a cross section that passes a center of each of the multiple projections in a plan view and that is perpendicular to the base member, and
the interval is more than or equal to 10 nm and less than or equal to 40 nm on a bottom portion side of the multiple projections.

5. The metal microscopic structure according to claim 1, wherein the metal film is made of gold, silver, copper, aluminum, or an alloy containing gold, silver, copper, or aluminum as a main component.

6. A detection device comprising the metal microscopic structure according to claim 1;
an inlet guide configured to introduce both a sample containing an analyte and a luminous body to the metal microscopic structure;
a light source capable of emitting light with which the metal microscopic structure and a bound body of the analyte and the luminous body are irradiated; and
an optical detector configured to detect light emitted from the luminous body that has been excited by the light emitted from the light source.

7. The detection device according to claim 6, further comprising:
a first antibody that has a property of specifically binding to the analyte and that has been immobilized onto the metal microscopic structure, wherein the analyte is a virus or a component of the virus; and
a second antibody that has a property of specifically binding to the analyte specifically bound to the first antibody and that has been labeled with the luminous body.

8. The detection device according to claim 6, wherein a wavelength of the light emitted from the light source is longer than or equal to 400 nm and shorter than or equal to 850 nm, and a wavelength of the light detected by the optical detector is longer than or equal to 400 nm and shorter than or equal to 850 nm.

9. The metal microscopic structure according to claim 1, wherein the second metal film has a smaller surface roughness than the first metal film.

10. The metal microscopic structure according to claim 1, wherein the film thickness of the metal film positioned in the bottom portion of the gap between every adjacent two of the multiple projections is more than or equal to 90% and less than 100% of the film thickness of the metal film deposited on the top portions of the multiple protrusions.

11. A metal microscopic structure comprising:
a base member including multiple protrusions arrayed at predetermined intervals; and
multiple projections made of a metal film covering the base member and configured to generate surface plasmons upon irradiation with light, wherein:
a film thickness of the metal film positioned in a bottom portion of a gap between every adjacent two of the multiple projections is greater than a height of the multiple protrusions and is more than or equal to 90% and less than or equal to 100% of a film thickness of the metal film deposited on top portions of the multiple protrusions,
the base member is made of resin,
each of the multiple protrusions has a circular columnar shape,
the multiple protrusions are arranged in a form of regular triangle lattices in a plan view,
a thickness of the multiple protrusions is more than or equal to 184 nm and less than or equal to 276 nm, and
an interval between every adjacent two of the multiple protrusions is more than or equal to 184 nm and less than or equal to 276 nm.

12. A metal microscopic structure comprising:
a base member including multiple protrusions arrayed at predetermined intervals; and
multiple projections made of a metal film covering the base member and configured to generate surface plasmons upon irradiation with light, wherein:
a film thickness of the metal film positioned in a bottom portion of a gap between every adjacent two of the multiple projections is greater than a height of the multiple protrusions and is more than or equal to 90% and less than or equal to 100% of a film thickness of the metal film deposited on top portions of the multiple protrusions,
the height of each of the multiple protrusions is more than or equal to 160 nm and less than or equal to 240 nm, and
the film thickness of the metal film positioned in the bottom portion of the gap between every adjacent two of the multiple projections is more than or equal to 200 nm and less than or equal to 600 nm.

13. A metal microscopic structure comprising:
a base member including multiple protrusions arrayed at predetermined intervals; and
multiple projections made of a metal film covering the base member and configured to generate surface plasmons upon irradiation with light, wherein:
a film thickness of the metal film positioned in a bottom portion of a gap between every adjacent two of the multiple projections is greater than a height of the multiple protrusions and is more than or equal to 90% and less than or equal to 100% of a film thickness of the metal film deposited on top portions of the multiple protrusions,
an interval between every adjacent two of the multiple projections is more than or equal to 40 nm and less than or equal to 120 nm on a top portion side of the multiple projections in a cross section that passes a center of each of the multiple projections in a plan view and that is perpendicular to the base member, and
the interval is more than or equal to 10 nm and less than or equal to 40 nm on a bottom portion side of the multiple projections.

\* \* \* \* \*